US005538998A

United States Patent [19]

Sugihara et al.

[11] Patent Number: 5,538,998
[45] Date of Patent: Jul. 23, 1996

[54] HALOPROPIOLAMIDE COMPOUND, PRODUCTION AND USE THEREOF

[75] Inventors: Yoshihiro Sugihara; Toshiro Yamashita; Sachio Shibata, all of Tsukuba; Koichi Matsumura; Yosei Kuwazuru, both of Osaka, all of Japan

[73] Assignee: Takeda Chemical Industries, Ltd., Osaka, Japan

[21] Appl. No.: 327,396

[22] Filed: Oct. 21, 1994

[30] Foreign Application Priority Data

| Oct. 22, 1993 | [JP] | Japan | 5-264836 |
| Oct. 22, 1993 | [JP] | Japan | 5-264837 |
| Mar. 29, 1994 | [JP] | Japan | 6-059156 |
| Mar. 29, 1994 | [JP] | Japan | 6-059157 |

[51] Int. Cl.$^6$ ............................ A01N 37/18; C07C 233/09
[52] U.S. Cl. ............................ 514/627; 514/628; 514/330; 564/192; 564/204; 564/205; 564/209; 546/245
[58] Field of Search ...................... 564/204, 192, 564/205; 514/627, 628

[56] References Cited

FOREIGN PATENT DOCUMENTS

| 0519427A2 | 12/1992 | European Pat. Off. . |
| 0552418A1 | 7/1993 | European Pat. Off. . |
| 53-17579 | 6/1978 | Japan . |
| 3-184960 | 8/1991 | Japan . |

OTHER PUBLICATIONS

Heinz Gunter Viehe, *Heterosubstituierte Acetylene (II.)*, pp. 1950–1956 (1992).
T. Sasaki et al., *Notes*, 43(4):1252–1254 (1970).
T. Sasaki et al., *J. Chem. Soc.* (C), pp. 406–408 (1969).

*Primary Examiner*—Shailendra Kumar
*Attorney, Agent, or Firm*—David G. Conlin; Peter F. Corless

[57] ABSTRACT

There are provided with a novel N-substituted-3-halopropiolamide compound, a method of producing the compound, and a composition for controlling noxious organisms containing the compound. The present compound exhibits superior antimicrobial and antifungal effects. Pest control agents containing the compound can advantageously be used for wide applications.

30 Claims, No Drawings

HALOPROPIOLAMIDE COMPOUND, PRODUCTION AND USE THEREOF

BACKGROUND OF THE INVENTION

The present invention relates to a novel N-substituted-3-halopropiolamide compound, a method of producing the same compound, and a composition for controlling noxious organisms containing the same compound.

It has been reported by Yamazoe et al. that certain propiolic acid derivatives and propiolamide derivatives exhibit antifungal activity [Japanese J. Pharmacology, Vol. 102, page 278 (1982)]. N-(substituted phenyl)propiolamide is known to exhibit bactericidal activity, wood preservative activity, and repelling activity for water microbial [disclosed in Japanese Patent Publication Nos. 14756/1965, 31220/1969, and 58885/1985, respectively]. It is also reported that 3-iodopropiolic acid (I—C≡C—COOH) and esters or derivatives thereof have exhibited antifungal activity [Ann. Applied Biol., Vol. 36, page 250 (1949); Japanese J. Pharmacology, Vol. 90, page 1578 (1970)]. The present patent assignee synthesized a large number of N-substituted-3-iodopropiolamides and reported that these compounds have antibacterial and antifungal activities [European Patent No. 0519427 (A1)].

On the other hand, 3-chloropropiolamide (Cl—C≡CONH$_2$), N-branched alkyl derivatives thereof and bridged ring alkyl-substituted derivatives thereof are known compounds, of which biological activities are not disclosed [J. Chem. Soc. C, (3), page 406 (1969); J. Chem. Soc. C, (11), page 2147 (1971); Japanese Patent Publication No. 17579/1978]. Further, 3-bromopropiolic acid (Br—C≡COOH$_2$) and methyl 3-bromopropiolate (Br—C≡CO$_2$CH$_3$) are known compounds, of which biological activities are not disclosed [Berichte, Vol. 63B, page 1868 (1930); J. Am. Chem. Soc., Vol. 71, page 2948 (1949); Ann. Chem., Vol. 2, page 819 (1957); Japanese Patent Publication No. 40402/1988; Synth. Comm., Vol. 22, page 567 (1992)].

Accordingly, an object of the present invention is to provide a novel compound which has a different chemical structure from those of the compounds disclosed in the above mentioned articles and patent gazettes, and which exhibits superior antibacterial and antifungal activities.

SUMMARY OF THE INVENTION

The present inventors have discovered novel N-substituted- 3-halopropiolamide compounds having superior and wide-ranging antibacterial and antifungal activities.

Compounds in accordance with the present invention have been discovered to exhibit superior antibacterial and antifungal activities against (1) gram-positive bacteria, such as *Staphylococcus aureus*, and *Bacillus subtilis*; (2) gram-negative bacteria such as *Pseudomonas aeruginosa* and *Escherichia coli*; (3) yeasts, such as *Saccharomyces cersvisiae* and *Candida albicans*; (4) fungus, such as aspergillus niger, *Penicillium citrinum, Cladosporium cladosporioides, Aureobasidium pullulans, Chaetomium globossum, Trichoderma viride*, and *Paecilomyces variotti*; and (5) wood rot fungi, such as *Tyromyces palustris* and *Coriolus versicolor*. In addition, compounds in accordance with the present invention are active as insecticides, such as an acaricide or a termiticide. Thus the present invention provides compounds and compositions for controlling a wide variety of noxious organisms. The compounds and compositions can be used as antibacterial/antifungal agents, agents for preventing deterioration of industrial products and industrial water, slime controlling agents, wood preservatives, and insacticides.

More specifically, the present invention is directed to a compound represented by the general formula:

$$\text{Hal—C≡C—CO—NR}_1\text{R}_2 \qquad (I)$$

wherein Hal is a chlorine atom or a bromine atom, and (i) when Hal is a chlorine atom, R$_1$ is a linear alkyl group optionally substituted by 1 through 4 substituents selected from the group consisting of (1) C$_{3-8}$ cycloalkyl, (2) halogen selected from the group consisting of fluorine, chlorine, and iodine, (3) cyano, (4) hydroxyl, (5) C$_{1-4}$ alkoxy, (6) carboxyl, (7) C$_{1-4}$ alkoxycarbonyl, (8) ketone, (9) nitro, (10) amino, (11) carbamoyl, (12) C$_{1-4}$ alkanoyl, and (13) five- to ten-membered aromatic heterocyclic group containing, other than the carbon atom(s), 1 through 4 hereto atoms selected from the group consisting of a nitrogen atom, an oxygen atom and a sulfur atom, the five- to ten-membered aromatic heterocyclic group being optionally substituted by C$_{1-4}$ alkyl, C$_{3-8}$ cycloalkyl, halogen, cyano, hydroxyl, C$_{1-4}$ alkoxy, carboxyl, C$_{1-4}$ alkoxycarbonyl, nitro, amino, carbamoyl, or C$_{1-4}$ alkanoyl; an optionally substituted alkenyl group; an optionally substituted alkynyl group; an optionally substituted cycloalkyl group; or an optionally substituted aromatic hydrocarbon group, and R$_2$ is a hydrogen atom or an optionally substituted hydrocarbon atom, in which R$_1$ and R$_2$ optionally form a ring in cooperation with a nitrogen atom adjacent thereto, and (ii) when Hal is a bromine atom, R$_1$ and R$_2$ are each a hydrogen atom or an optionally substituted hydrocarbon group, in which R$_1$ and R$_2$ optionally form a ring in cooperation with a nitrogen atom adjacent thereto.

The present invention is also directed to a method of producing the compound (I) and a composition for controlling noxious organisms containing a compound represented by the general formula:

$$\text{Hal—C≡C—CO—NR}_1'\text{R}_2 \qquad (I')$$

wherein Hal is a chlorine atom or a bromine atom, a (i) when Hal is a chlorine atom, R$_1$' is an optionally substituted linear alkyl group; an optionally substituted alkenyl group; an optionally substituted alkynyl group; an optionally substituted cycloalkyl group; or an optionally substituted aromatic hydrocarbon group, and R$_2$ is a hydrogen atom or an optionally substituted hydrocarbon atom, in which R$_1$' and R$_2$ optionally form a ring in cooperation with a nitrogen atom adjacent thereto, and (ii) when Hal is a bromine atom, R$_1$' and R$_2$ are each a hydrogen atom or an optionally substituted hydrocarbon group, in which R$_1$' and R$_2$ optionally form a ring in cooperation with a nitrogen atom adjacent thereto.

The compound (I') having an effect of controlling noxious organisms according to the present invention contains an N-substituted-3-chloropropiolamide compound represented by the general formula:

$$\text{Cl—C≡C—CO—NR}_3'\text{R}_4 \qquad (Ia')$$

wherein R$_3$' is an optionally substituted linear alkyl group, an optionally substituted alkenyl group, an optionally substituted alkynyl group, an optionally substituted cycloalkyl group, or an optionally substituted aromatic hydrocarbon group, and R$_4$ is a hydrogen atom or an optionally substituted hydrocarbon atom, in which R$_3$' and R$_4$ optionally form a ring in cooperation with a nitrogen atom adjacent thereto, and contains an N-substituted-3-bromopropiolamide compound represented by the general formula:

$$Br-C\equiv C-CO-NR_5NR_6 \qquad (Ib)$$

wherein $R_5$ and $R_6$ are each a hydrogen atom, or an optionally substituted hydrocarbon group, in which $R_5$ and $R_6$ optionally form a ring in cooperation with a nitrogen atom adjacent thereto. Of the above mentioned compounds, the N-substituted-3-chloropropiolamide compound having the general formula:

$$Cl-C\equiv C-CO-NR_3R_4 \qquad (Ia)$$

and the compound (Ib) are novel compounds, wherein $R_3$ is a linear alkyl group optionally substituted by 1 through 4 substituents selected from the group consisting of (1) $C_{3-8}$ cycloalkyl, (2) fluorine, chlorine or iodine, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, (12) $C_{1-4}$ alkanoyl, and (13) five- to ten-membered aromatic heterocyclic group containing, other than the carbon atom(s), 1 through 4 hetero atoms selected from the group consisting of a nitrogen atom, an oxygen atom and a sulfur atom, the five- to ten-membered aromatic heterocyclic group being optionally substituted by $C_{1-4}$ alkyl, $C_{3-8}$ cycloalkyl, halogen, cyano, hydroxyl, $C_{1-4}$ alkoxy, carboxyl, $C_{1-4}$ alkoxycarbonyl, nitro, amino, carbamoyl, or $C_{1-4}$ alkanoyl; an optionally substituted alkenyl group; an optionally substituted alkynyl group; an optionally substituted cycloalkyl group; or an optionally substituted aromatic hydrocarbon group, and $R_4$ is a hydrogen atom or an optionally substituted hydrocarbon atom, in which $R_3$ and $R_4$ optionally form a ring in cooperation with a nitrogen atom adjacent thereto.

More specifically, following [1] through [63] are provided.

[1] A compound represented by the general formula:

$$Hal-C\equiv C-CO-NR_1R_2 \qquad (I)$$

wherein Hal is a chlorine atom or a bromine atom, and (i) when Hal is a chlorine atom, $R_1$ is a linear alkyl group optionally substituted by 1 through 4 substituents selected from the group consisting of (1) $C_{3-8}$ cycloalkyl, (2) halogen selected from the group consisting of fluorine, chlorine, and iodine, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, (12) $C_{1-4}$ alkanoyl, and (13) five- to ten-membered aromatic heterocyclic group containing, other than the carbon atom(s), 1 through 4 hetero atoms selected from the group consisting of a nitrogen atom, an oxygen atom and a sulfur atom, the five- to ten-membered aromatic heterocyclic group being optionally substituted by $C_{1-4}$ alkyl, $C_{3-8}$ cycloalkyl, halogen, cyano, hydroxyl, $C_{1-4}$ alkoxy, carboxyl, $C_{1-4}$ alkoxycarbonyl, nitro, amino, carbamoyl, or $C_{1-4}$ alkanoyl; an optionally substituted alkenyl group; an optionally substituted alkynyl group; an optionally substituted cycloalkyl group; or an optionally substituted aromatic hydrocarbon group, and $R_2$ is a hydrogen atom or an optionally substituted hydrocarbon group, in which $R_1$ and $R_2$ optionally form a ring in cooperation with a nitrogen atom adjacent thereto, and (ii) when Hal is a bromine atom, $R_1$ and $R_2$ are each a hydrogen atom or an optionally substituted hydrocarbongroup, in which $R_1$ and $R_2$ optionally form a ring in cooperation with a nitrogen atom adjacent thereto.

[2] A compound as disclosed in [1] represented by the general formula:

$$Cl-C\equiv C-CO-NR_3R_4 \qquad (Ia)$$

wherein $R_3$ is a linear alkyl group optionally substituted by 1 through 4 substituents selected from the group consisting of (1) $C_{3-8}$ cycloalkyl, (2) halogen selected from the group consisting of fluorine, chlorine, and iodine, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, (12) $C_{1-4}$ alkanoyl, and (13) five- to ten-membered aromatic heterocyclic group containing, other than the carbon atom(s), 1 through 4 hetero atoms selected from the group consisting of a nitrogen atom, an oxygen atom and a sulfur atom, the five- to ten-membered aromatic heterocyclic group being optionally substituted by $C_{1-4}$ alkyl, $C_{3-8}$ cycloalkyl, halogen, cyano, hydroxyl, $C_{1-4}$ alkoxy, carboxyl, $C_{1-4}$ alkoxycarbonyl, nitro, amino, carbamoyl, or $C_{1-4}$ alkanoyl; an optionally substituted alkenyl group; an optionally substituted alkynyl group; an optionally substituted cycloalkyl group; or an optionally substituted aromatic hydrocarbon group, and $R_4$ is a hydrogen atom or an optionally substituted hydrocarbon atom, in which $R_3$ and $R_4$ optionally form a ring in cooperation with a nitrogen atom adjacent thereto.

[3] A compound as disclosed in [2] wherein the optionally substituted alkenyl group represented by $R_3$ is a linear or branched $C_{2-24}$ alkenyl group, the linear or branched alkenyl group being optionally substituted by 1 through 4 substituents selected from the group consisting of (1) $C_{3-8}$ cycloalkyl, (2) halogen, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, and (12) $C_{1-4}$ alkanoyl.

[4] A compound as disclosed in [2] wherein the optionally substituted alkynyl group represented by $R_3$ is a linear or branched $C_{2-24}$ alkynyl group, the linear or branched alkynyl group being optionally substituted by 1 through 4 substituents selected from the group consisting of (1) $C_{3-8}$ cycloalkyl, (2) halogen, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, and (12) $C_{1-4}$ alkanoyl.

[5] A compound as disclosed in [2] wherein the optionally substituted cycloalkyl represented by $R_3$ is a $C_{3-8}$ cycloalkyl group, the cycloalkyl group being optionally substituted by 1 through 4 substituents selected from the group consisting of (1) $C_{1-4}$ alkyl, (2) halogen, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, and (12) $C_{1-4}$ alkanoyl.

[6] A compound as disclosed in [2] wherein the optionally substituted aromatic hydrocarbon group represented by $R_3$ is:

(i) a $C_{6-18}$ aryl group, the aryl group being optionally substituted by 1 through 4 substituents selected from the group consisting of (1) a $C_{1-4}$ alkyl, the alkyl being optionally substituted by a halogen atom, (2) $C_{3-8}$ cycloalkyl, (3) halogen, (4) cyano, (5) hydroxyl, (6) $C_{1-4}$ alkoxy, (7) carboxyl, (8) $C_{1-4}$ alkoxycarbonyl, (9) nitro, (10) amino, (11) carbamoyl, and (12) $C_{1-4}$ alkanoyl; or (ii) a $C_{1-24}$ alkyl group substituted by $C_{6-18}$ aryl, the each of $C_{1-24}$ alkyl group and $C_{6-8}$ aryl group being optionally substituted by 1 through 4 substituents selected from the group consisting of (1) a $C_{1-4}$ alkyl group, the alkyl group being optionally substituted by a halogen atom, (2) $C_{3-8}$ cycloalkyl, (3) halogen, (4) cyano, (5) hydroxyl, (6) $C_{1-4}$ alkoxy, (7) carboxyl, (8) $C_{1-4}$ alkoxycarbonyl, (9) nitro, (10) amino, (11) carbamoyl, and (12) $C_{1-4}$ alkanoyl.

[7] A compound as disclosed in [2] wherein $R_3$ is an unsubstituted linear $C_{1-24}$ alkyl group, an optionally substituted alkenyl group, an optionally substituted alkynyl group, an optionally substituted cycloalkyl group, or an optionally substituted aromatic hydrocarbon group.

[8] A compound as disclosed in [2] wherein $R_3$ is a linear $C_{1-24}$ alkyl group, the linear alkyl group being optionally substituted by 1 through 4 substituents selected from the group consisting of (1) $C_{3-8}$ cycloalkyl, (2) halogen selected from the group consisting of fluorine, chlorine, and iodine, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, (12) $C_{1-4}$ alkanoyl, and (13) a five- to ten-membered aromatic heterocyclic group containing, other than the carbon atom(s), 1 through 4 hetero atoms selected from the group consisting of a nitrogen atom, an oxygen atom and a sulfur atom, the five- to ten-membered aromatic heterocyclic group being optionally substituted by $C_{1-4}$ alkyl, $C_{3-8}$ cycloalkyl, halogen, cyano, hydroxyl, $C_{1-4}$ alkoxy, carboxyl, $C_{1-4}$ alkoxycarbonyl, nitro, amino, carbamoyl, or $C_{1-4}$ alkanoyl; or an optionally substituted phenyl group.

[9] A compound as disclosed in [2] wherein the hydrocarbon group of the optionally substituted hydrocarbon group represented by $R_4$ is a $C_{1-24}$ alkyl group, a $C_{3-8}$ cycloalkyl group, a $C_{2-24}$ alkenyl group, a $C_{2-24}$ alkynyl group, a $C_{6-18}$ aryl group, or a $C_{1-24}$ alkyl substituted by $C_{6-18}$ aryl.

[10] A compound as disclosed in [2] wherein the optionally substituted hydrocarbon group represented by $R_4$ is:

(i) a linear or branched $C_{1-24}$ alkyl group, the linear or branched alkyl group being optionally substituted by 1 through 4 substituents selected from the group consisting of (1) $C_{3-8}$ cycloalkyl, (2) halogen, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, (12) $C_{1-4}$ alkanoyl, and (13) a five- to ten-membered aromatic heterocyclic group containing, other than the carbon atom(s), 1 through 4 hetero atoms selected from the group consisting of a nitrogen atom, an oxygen atom and a sulfur atom, the five- to ten-membered aromatic heterocyclic group being optionally substituted by $C_{1-4}$ alkyl, $C_{3-8}$ cycloalkyl, halogen, cyano, hydroxyl, $C_{1-4}$ alkoxy, carboxyl, $C_{1-4}$ alkoxycarbonyl, nitro, amino, carbamoyl, or $C_{1-4}$ alkanoyl;

(ii) a linear or branched $C_{2-24}$ alkenyl group, the linear or branched alkenyl group being optionally substituted by 1 through 4 substituents selected from the group consisting of (1) $C_{3-8}$ cycloalkyl, (2) halogen, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, and (12) $C_{1-4}$ alkanoyl;

(iii) a linear or branched $C_{2-24}$ alkynyl group, the linear or branched alkynyl group being optionally substituted by 1 through 4 substituents selected from the group consisting of (1) $C_{3-8}$ cycloalkyl, (2) halogen, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, and (12) $C_{1-4}$ alkanoyl;

(iv) a $C_{3-8}$ cycloalkyl group, the $C_{3-8}$ cycloalkyl group being optionally substituted by 1 through 4 substituents selected from the group consisting of (1) $C_{1-4}$ alkyl, (2) halogen, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, and (12) $C_{1-4}$ alkanoyl;

(v) a $C_{6-18}$ aryl group, the $C_{6-18}$ aryl group being optionally substituted by 1 through 4 substituents selected from the group consisting of (1) a $C_{1-4}$ alkyl group, the $C_{1-4}$ alkyl group being optionally substituted by a halogen atom, (2) $C_{3-8}$ cycloalkyl, (3) halogen, (4) cyano, (5) hydroxyl, (6) $C_{1-4}$ alkoxy, (7) carboxyl, (8) $C_{1-4}$ alkoxycarbonyl, (9) nitro, (10) amino, (11) carbamoyl, and (12) $C_{1-4}$ alkanoyl; or (vi) a $C_{1-24}$ alkyl group and substituted by $C_{6-18}$ aryl, each of the $C_{1-24}$ alkyl group and the $C_{6-18}$ aryl group being optionally substituted by 1 through 4 substituents selected from the group consisting of (1) a $C_{1-4}$ alkyl group, the alkyl group being optionally substituted by a halogen atom, (2) $C_{3-8}$ cycloalkyl, (3) halogen, (4) cyano, (5) hydroxyl, (6) $C_{1-4}$ alkoxy, (7) carboxyl, (8) $C_{1-4}$ alkoxycarbonyl, (9) nitro, (10) amino, (11) carbamoyl, and (12) $C_{1-4}$ alkanoyl.

[11] A compound as disclosed in any one of [1] through [10] wherein $R_4$ is a hydrogen atom.

[12] A compound as disclosed in [2] wherein the ring formed by $R_3$ and $R_4$ in cooperation with a nitrogen atom adjacent thereto is a five- to eight-membered nitrogen-containing ring or a fused ring of said nitrogen-containing ring and another ring, and the nitrogen-containing ring or the fused ring containing, other than the nitrogen atom, 1 through 4 atoms selected from the group consisting of a carbon atom, a nitrogen atom, an oxygen atom and a sulfur atom, the ring being optionally substituted by 1 through 4 substituents selected from the group consisting of (1) $C_{1-4}$ alkyl, (2) $C_{3-8}$ cycloalkyl, (3) halogen, (4) cyano, (5) hydroxyl, (6) $C_{1-4}$ alkoxy, (7) carboxyl, (8) $C_{1-4}$ alkoxycarbonyl, (9) ketone, (10) nitro, (11) amino, (12) carbamoyl, (13) $C_{1-4}$ alkanoyl, and (14) $C_{6-18}$ aryl.

[13] A compound as disclosed in [2] wherein $R_3$ is a linear $C_{1-18}$ alkyl group and $R_4$ is a hydrogen atom.

[14] A compound as disclosed in [2] wherein $R_3$ is a linear $C_{1-18}$ alkyl group and $R_4$ is a $C_{1-18}$ alkyl group.

[15] A compound as disclosed in [2] wherein $R_3$ is a linear $C_{1-6}$ alkyl group and $R_4$ is a linear or branched $C_{1-6}$ alkyl group.

[16] A compound as disclosed in [2] wherein $R_3$ is a $C_{6-18}$ aryl group, the $C_{6-18}$ aryl group being optionally substituted by 1 through 4 substituents selected from the group consisting of (1) a $C_{1-4}$ alkyl group, the alkyl group being optionally substituted by a halogen atom, (2) $C_{3-8}$ cycloalkyl, (3) halogen, (4) cyano, (5) hydroxyl, (6) $C_{1-4}$ alkoxy, (7) carboxyl, (8) $C_{1-4}$ alkoxycarbonyl, (9) nitro, (10) amino, (11) carbamoyl, and (12) $C_{1-4}$ alkanoyl, and $R_4$ is a hydrogen atom.

[17] A compound as disclosed in [16] wherein $R_3$ is a phenyl group optionally substituted by halogen, trifluoromethyl, or nitro, and $R_4$ is a hydrogen atom.

[18] A compound as disclosed in [2] wherein $R_3$ is a $C_{3-8}$ cycloalkyl group, and $R_4$ is a hydrogen atom.

[19] A compound as disclosed in [2] wherein a cyclic amino group represented by —$NR_3R_4$ when $R_3$ and $R_4$ form a ring in cooperation with a nitrogen atom adjacent thereto is 1-pyrrolidyl, 1-imidazolyl, piperidino (1-piperidyl), 1-piperazinyl, 3-oxazolidinyl, hexamethylenimino, heptamethylenimino, morpholino (4-morpholinyl), or 1-indolinyl.

[20] A compound as disclosed in [2] wherein a cyclic amino group represented by —NR3$R_4$ when $R_3$ and $R_4$ form a ring in cooperation with a nitrogen atom adjacent thereto is piperidino (1-piperidyl).

[21] A compound as disclosed in [2] wherein the compound is N-(n-hexyl)-3-chloropropiolamide, N-(n-heptyl)-3-chloropropiolamide, N-(n-octyl)-3chloropropiolamide, N-(n-nonyl)-3-chloropropiolamide, N-(n-decyl)-3-chloropropiolamide, N-(n-pentyl)-3-chloropropiolamide, N-methyl-3-chloropropiolamide, N-ethyl- 3-chloropropiolamide, N-propyl-3-chloropropiolamide, N-butyl-3-chloropropiolamide, N-dodecyl- 3-chloropropiolamide, N-tetradecyl-3-chloropropiolamide, N-octadecyl-3-chloropropiolamide, N-(m-chlorophenyl)-3-chloropropiolamide, N-(p-chlorophenyl)- 3-chloropropiolamide, N-(m-trifluoromethylphenyl)- 3-chloropropiolamide, N-(m-nitrophenyl)- 3-chloropropiolamide, N-(2,4-dichlorophenyl)-3-chloropropiolamide, N,N-dimethyl-3-chloropropiolamide, N,N-dibutyl-3-chloropropiolamide, 1-(3-chloropropioloyl)piperidine, or N-cyclohexyl-3-chloropropiolamide.

[22] A compound as disclosed in [1] represented by the general formula:

$$Br-C\equiv C-CO-NR_5R_6 \qquad (Ib)$$

wherein $R_5$ and $R_6$ are each a hydrogen atom, or an optionally substituted hydrocarbon group, in which $R_5$ and $R_6$ optionally form a ring in cooperation with a nitrogen atom adjacent thereto.

[23] A compound as disclosed in [22] wherein the hydrocarbon group of the optionally substituted hydrocarbon group represented by $R_5$ and $R_6$ is a $C_{1-24}$ alkyl, a $C_{3-8}$ cycloalkyl group, a $C_{2-24}$ alkenyl group, a $C_{2-24}$ alkynyl group, a $C_{6-18}$ aryl group, or a $C_{1-24}$ alkyl group substituted by $C_{6-18}$ aryl.

[24] A compound as disclosed in [22] wherein the optionally substituted hydrocarbon group represented by $R_5$ and $R_6$ is (i) a $C_{1-24}$ alkyl group, the $C_{1-24}$ alkyl group being optionally substituted by 1 through 4 substituents selected from the group consisting of (1) $C_{3-8}$ cycloalkyl, (2) halogen, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, (12) $C_{1-4}$ alkanoyl, and (13) five- to ten-membered aromatic heterocyclic group containing, other than the carbon atom(s), 1 through 4 hetero atoms selected from the group consisting of a nitrogen atom, an oxygen atom and a sulfur atom, the five- to ten-membered aromatic heterocyclic group being optionally substituted by $C_{1-4}$ alkyl, $C_{3-8}$ cycloalkyl, halogen, cyano, hydroxyl, $C_{1-4}$ alkoxy, carboxyl, $C_{1-4}$ alkoxycarbonyl, nitro, amino, carbamoyl, or $C_{1-4}$ alkanoyl;

(ii) a linear or branched $C_{2-24}$ alkenyl group, the linear or branched $C_{2-24}$ alkenyl group being optionally substituted by 1 through 4 substituents selected from the group consisting of (1) $C_{3-8}$ cycloalkyl, (2) halogen, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, and (12) $C_{1-4}$ ' alkanoyl;

(iii) a linear or branched $C_{2-24}$ alkynyl group, the linear or branched alkynyl group being optionally substituted by 1 through 4 substituents selected from the group consisting of (1) $C_{3-8}$ cycloalkyl, (2) halogen, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, and (12) $C_{1-4}$ alkanoyl;

(iv) a $C_{3-8}$ cycloalkyl group, the $C_{3-8}$ cycloalkyl group being optionally substituted by 1 through 4 substituents selected from the group consisting of (1) $C_{1-4}$ alkyl, (2) halogen, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, and (12) $C_{1-4}$ alkanoyl;

(v) a $C_{6-18}$ aryl group, the $C_{6-18}$ aryl group being optionally substituted by 1 through 4 substituents selected from the group consisting of (1) a $C_{1-4}$ alkyl group optionally substituted by a halogen atom, (2) $C_{3-8}$ cycloalkyl, (3) halogen, (4) cyano, (5) hydroxyl, (6) $C_{1-4}$ alkoxy, (7) carboxyl, (8) $C_{1-4}$ alkoxycarbonyl, (9) nitro, (10) amino, (11) carbamoyl, and (12) $C_{1-14}$ alkanoyl; or (vi) a $C_{1-24}$ alkyl group substituted by $C_{6-18}$ aryl, each of the $C_{1-24}$ alkyl group and the $C_{6-8}$ aryl group being optionally substituted by 1 through 4 substituents selected from the group consisting of (1) a $C_{1-4}$ alkyl group optionally substituted by a halogen atom, (2) $C_{3-8}$ cycloalkyl, (3) halogen, (4) cyano, (5) hydroxyl, (6) $C_{1-4}$ alkoxy, (7) carboxyl, (8) $C_{1-4}$ alkoxycarbonyl, (9) nitro, (10) amino, (11) carbamoyl, and (12) $C_{1-4}$ alkanoyl.

[25] A compound as disclosed in [22] wherein the ring formed by $R_5$ and $R_6$ in cooperation with a nitrogen atom adjacent thereto is a five- to eight membered nitrogen-containing ring or a fused ring of said nitrogen-containing ring and another ring, and the nitrogen-containing ring or the fused ring containing, other than the nitrogen atom, 1 through 4 hetero atoms selected from the group consisting of a carbon atom, a nitrogen atom, an oxygen atom and a sulfur atom, the ring being optionally substituted by 1 through 4 substituents selected from the group consisting of (1) $C_{1-4}$ alkyl, (2) $C_{3-8}$ cycloalkyl, (3) halogen, (4) cyano, (5) hydroxyl, (6) $C_{1-4}$ alkoxy, (7) carboxyl, (8) $C_{1-4}$ alkoxycarbonyl, (9) ketone, (10) nitro, (11) amino, (12) carbamoyl, (13) $C_{1-4}$ alkanoyl, and (14) $C_{6-18}$ aryl.

[26] A compound as disclosed in [22] wherein $R_5$ is an optionally substituted linear $C_{1-18}$ alkyl group or an optionally substituted phenyl group.

[27] A compound as disclosed in any one of [22] through [26] wherein $R_6$ is a hydrogen atom.

[28] A compound as disclosed in [22] wherein $R_5$ and $R_6$ are each a hydrogen atom.

[29] A compound as disclosed in [22] wherein $R_5$ is a $C_{1-18}$ alkyl group and $R_6$ is a hydrogen atom.

[30] A compound as disclosed in [22] wherein $R_5$ is a $C_{1-18}$ alkyl group, the alkyl group being optionally substituted by 1 through 4 substituents selected from the group consisting of (1) $C_{3-8}$ cycloalkyl, (2) halogen, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, (12) $C_{1-4}$ alkanoyl, and (13) five- to ten-membered aromatic heterocyclic group containing, other than the carbon atom(s), 1 through 4 hetero atoms selected from the group consisting of a nitrogen atom, an oxygen atom and a sulfur atom, the five- to ten-membered aromatic heterocyclic group being optionally substituted by $C_{1-4}$ alkyl, $C_{3-8}$ cycloalkyl, halogen, cyano, hydroxyl, $C_{1-4}$ alkoxy, carboxyl, $C_{1-4}$ alkoxycarbonyl, nitro, amino, carbamoyl, or $C_{1-4}$ alkanoyl, and $R_6$ is a hydrogen atom.

[31] A compound as disclosed in [22] wherein $R_5$ is a $C_{1-18}$ alkyl group, and $R_6$ is a $C_{1-18}$ alkyl group.

[32] A compound as disclosed in [22] wherein $R_5$ is a $C_{1-6}$ alkyl group, and $R_6$ is a $C_{1-6}$ alkyl group.

[33] A compound as disclosed in [22] wherein $R_5$ is a $C_{6-18}$ aryl group, the aryl group being optionally substituted by 1 through 4 substituents selected from the group consisting of (1) a $C_{1-4}$ alkyl group, the $C_{1-4}$ alkyl group being optionally substituted by a halogen atom, (2) $C_{3-8}$ cycloalkyl, (3) halogen, (4) cyano, (5) hydroxyl, (6) $C_{1-4}$ alkoxy, (7) carboxyl, (8) $C_{1-4}$ alkoxycarbonyl, (9) nitro, (10) amino, (11) carbamoyl, and (12) $C_{1-4}$ alkanoyl, and $R_6$ is a hydrogen atom.

[34] A compound as disclosed in [22] wherein $R_5$ is a phenyl group optionally substituted by halogen, trifluoromethyl, or nitro, and $R_6$ is a hydrogen atom.

[35] A compound as disclosed in [22] wherein $R_5$ is a $C_{3-8}$ cycloalkyl group, and $R_6$ is a hydrogen atom.

[36] A compound as disclosed in [22] wherein a cyclic amino group represented by —NR5R6 when R5 and R6 form a ring in cooperation with a nitrogen atom adjacent thereto is 1-pyrrolidyl, 1-imidazolyl, piperidino (1-piperidyl), 1-piperazinyl, 3-oxazolidinyl, hexamethylenimino, heptamethylenimino, morpholino (4-morpholinyl), or 1-indolinyl.

[37] A compound as disclosed in [22] wherein a cyclic amino group represented by —NR5R6 when R5 and R6 form a ring in cooperation with a nitrogen atom adjacent thereto is piperidino (1-piperidyl).

[38] A compound as disclosed in [22] wherein the compound is N-(tert- butyl)-3-bromopropiolamide, N-(n-hexyl)-3-bromopropiolamide, N-(n-heptyl)-3-bromopropiolamide, N-(n- octyl)-3-bromopropiolamide, N-(n-nonyl)-3-bromopropiolamide, N-(n-decyl)-3-bromopropiolamide, 3-bromopropiolamide, N-methyl-3-bromopropiolamide, N-ethyl-3-bromopropiolamide, N-propyl- 3-bromopropiolamide, N-butyl-3-bromopropiolamide, N-pentyl-3-bromopropiolamide, N-dodecyl- 3-bromopropiolamide, N-tetradecyl-3-bromopropiolamide, N-octadecyl-3-bromopropiolamide, N-(m-chlorophenyl)-3-bromopropiolamide, N-(p-chlorophenyl)- 3-bromopropiolamide, N-(m-trifluoromethylphenyl)- 3-bromopropiolamide, N-(m-nitrophenyl)-3-bromopropiolamide, N-(2,4-dichlorophenyl)- 3-bromopropiolamide, N-(2-pyridyl(ethyl))- 3-bromopropiolamide, N,N-dimethyl-3-bromopropiolamide, N,N-dibutyl-3-bromopropiolamide, 1-(3-bromopropioloyl)piperidine, or N-cyclohexyl-3-bromopropiolamide.

[39] A method of producing a compound disclosed in [2] comprising the step of:

chlorinating a compound having the general formula H—C≡C—CO—NR$_3$R$_4$, wherein R$_3$ is a linear alkyl group optionally substituted by 1 through 4 substituents selected from the group consisting of (1) C$_{3-8}$ cycloalkyl, (2) halogen selected from the group consisting of fluorine, chlorine, and iodine, (3) cyano, (4) hydroxyl, (5) C$_{1-4}$ alkoxy, (6) carboxyl, (7) C$_{1-4}$ alkoxycarbonyl, (8) ketone, (9) nitro, (10) amino, (11) carbamoyl, (12) C$_{1-4}$ alkanoyl, and (13) five- to ten-membered aromatic heterocyclic group containing, other than the carbon atom(s), 1 through 4 hetero atoms selected from the group consisting of a nitrogen atom, an oxygen atom and a sulfur atom, the five- to ten-membered aromatic heterocyclic group being optionally substituted by C$_{1-4}$ alkyl, C$_{3-8}$ cycloalkyl, halogen, cyano, hydroxyl, C$_{1-4}$ alkoxy, carboxyl, C$_{1-4}$ alkoxycarbonyl, nitro, amino, carbamoyl, or C$_{1-4}$ alkanoyl; an optionally substituted alkenyl group; an optionally substituted alkynyl group; an optionally substituted cycloalkyl group; or an optionally substituted aromatic hydrocarbon group, and R$_4$ is a hydrogen atom or an optionally substituted hydrocarbon atom, in which R$_3$ and R$_4$ optionally form a ring in cooperation with a nitrogen atom adjacent thereto; or amidating 3-chloropropiolic acid, a salt or a halogenide thereof with an amine compound having the general formula HNR$_3$R$_4$, wherein R$_3$ and R$_4$ are similar to those defined above; or dehydrohalogenating a compound having the general formula ClXC=CY—CO—NR$_3$R$_4$, wherein R$_3$ and R$_4$are similar to those defined above, X is a chlorine atom and Y is a hydrogen atom, or X is a hydrogen atom and Y is a chlorine atom, a bromine atom, or an iodine atom.

[40] A method of producing a compound disclosed in [22] comprising the step of:

brominating a compound having the general formula H—C≡C—CO—NR$_5$R$_6$, wherein R$_5$ and R$_6$ are each a hydrogen atom, or an optionally substituted hydrocarbon group, in which R$_5$ and R$_6$ optionally form a ring in cooperation with a nitrogen atom adjacent thereto; or amidating 3-bromopropiolic acid, a salt or a halogenide thereof with an amine compound having the general formula HNR$_5$R$_6$, wherein R$_5$ and R$_6$ are similar to those defined above; or dehydrohalogenating a compound having the general formula BrXC=CY—CO—NR$_5$R$_6$, wherein R$_5$ and R$_6$ are similar to those defined above, X is a bromine atom and Y is a hydrogen atom, or X is a hydrogen atom and Y is a chlorine atom, a bromine atom, or an iodine atom.

[41] A composition for controlling noxious organisms which comprises a compound represented by the general formula:

$$\text{Hal—C}\equiv\text{C—CO—NR}_1'\text{R}_2 \qquad (I')$$

wherein Hal is a chlorine atom or a bromine atom, and (i) when Hal is a chlorine atom, R$_1$' is an optionally substituted linear alkyl group; an optionally substituted alkenyl group; an optionally substituted alkynyl group; an optionally substituted cycloalkyl group; or an optionally substituted aromatic hydrocarbon group, and R$_2$ is a hydrogen atom or an optionally substituted hydrocarbon atom, in which R$_1$' and R$_2$ optionally form a ring in cooperation with a nitrogen atom adjacent thereto, and (ii) when Hal is a bromine atom, R$_1$' and R$_2$ are each a hydrogen atom or an optionally substituted hydrocarbon group, in which R$_1$' and R$_2$ optionally form a ring in cooperation with a nitrogen atom adjacent thereto.

[42] The composition for controlling noxious organisms as disclosed in [41] wherein the compound (I') is the compound disclosed in any one of [1] through [38].

[43] The composition for controlling noxious organisms as disclosed in [41] or [42] wherein the composition is an antiblastic composition, an antifungal composition, an insecticide, an acaricide or a termiticide.

[44] The composition for controlling noxious organisms as disclosed in [41] or [42] wherein the composition is a composition for preventing deterioration of wood.

[45] The composition for controlling noxious organisms as disclosed in [41] or [42] wherein the composition is an antideterioration for industrial water.

[46] An antibacterial composition that kills or inhibits the growth of gram-positive bacterium, which comprises the compound disclosed in [2] wherein R$_3$ is a linear C$_{1-10}$ alkyl group and R$_4$ is a hydrogen atom (corresponding to compounds in Examples 1 through 10 below), and preferably containing a compound disclosed in [2] wherein R$_3$ is a linear C$_{8-10}$ alkyl group, and R$_4$ is a hydrogen atom (corresponding to compounds in Examples 1 through 5 below).

[47] An antibacterial composition that kills or inhibits the growth of gram-negative bacterium, which comprises the compound disclosed in [2] wherein R$_3$ is a methyl group, and R$_4$ is a hydrogen atom (corresponding to compounds in Example 7 below).

[48] An antifungal composition which comprises the containing a compound disclosed in [2] wherein R$_3$ is a linear C$_{1-10}$ alkyl group and R$_4$ is a hydrogen atom (corresponding to compounds in Examples 1 through 10 below).

[49] An antibacterial composition that kills or inhibits the growth of gram-positive bacterium, the which comprises the a compound disclosed in [2] wherein R$_3$ is a phenyl group substituted by chlorine, a trifluoromethyl group or a nitro group, and R$_4$ is a hydrogen atom (such as compounds in Examples 14 through 18 below).

11

[50] An antifungal composition which comprises the compound disclosed in [2] wherein $R_3$ is a phenyl group substituted by chlorine, a trifluoromethyl group or a nitro group, and $R_4$ is a hydrogen atom (such as compounds in Examples 14 through 18 below).

[51] An antibacterial composition that kills or inhibits the growth of gram-positive bacterium which comprises the compound disclosed in [2] wherein $R_3$ and $R_4$ are each a methyl group, or $R_3$ and $R_4$ form a 1-piperidyl group in cooperation with a nitrogen atom adjacent thereto (such as compounds in Examples 19 and 21 below).

[52] An antifungal composition which comprises the compound disclosed in [2] wherein $R_3$ and $R_4$ are each a methyl group, or $R_3$ and $R_4$ form a 1-piperidyl group in cooperation with a nitrogen atom adjacent thereto (such as compounds in Examples 19 and 21 below).

[53] An antibacterial composition that kills or inhibits the growth of gram-positive bacterium, which comprises the compound disclosed in [22] wherein $R_5$ is a hydrogen atom or a linear $C_{1-10}$ alkyl group, and $R_6$ is a hydrogen atom (corresponding to compounds in Examples 24 through 34 below), and preferably containing a compound disclosed in [22] wherein $R_5$ is a hydrogen atom or a linear $C_{1-9}$ alkyl group, and $R_6$ is a hydrogen atom (corresponding to compounds in Examples 24 through 27 and 29 through 34 below).

[54] An antibacterial composition that kills or inhibits the growth of gram-negative bacterium which comprises the compound disclosed in [22] wherein $R_5$ is a hydrogen atom or a methyl group, and $R_6$ is a hydrogen atom (corresponding to compounds in Examples 29 and 30).

[55] Antifungal composition which comprises the compound disclosed in [22] wherein $R_5$ is a hydrogen atom or a linear $C_{1-10}$ alkyl group, and $R_6$ is a hydrogen atom (corresponding to compounds in Examples 24 through 34 below).

[56] An antibacterial composition that kills or inhibits the growth of gram-positive bacterium which comprises the compound disclosed in [22] wherein $R_5$ is a phenyl group substituted by chlorine, a trifluoromethyl group, or a nitro group, and $R_6$ is a hydrogen atom (such as compounds in Examples 38 through 42 below).

[57] An antifungal which comprises the compound disclosed in [22] wherein $R_5$ is a phenyl group substituted by chlorine, a trifluoromethyl group, or a nitro group, and $R_6$ is a hydrogen atom (such as compounds in Examples 38 through 42 below).

[58] An antibacterial composition that kills or inhibits the growth of gram-positive bacterium which comprises the compound disclosed in [22] wherein $R_5$ and $R_6$ are each a methyl group, or $R_5$ and $R_6$ form a 1-piperidyl group in cooperation with a nitrogen atom adjacent thereto (such as compounds in Examples 44 and 46 below).

[59] An antifungal which comprises the compound disclosed in [22] wherein $R_5$ and $R_6$ are each a methyl group, or $R_5$ and $R_6$ form a 1-piperidyl group in cooperation with a nitrogen atom adjacent thereto (such as compounds in Examples 44 and 46 below).

[60] A method of controlling noxious organisms comprising the step of applying an effective amount of a compound represented by the general formula:

$$Hal—C≡C—CO—NR_1'R_2 \tag{I'}$$

wherein Hal is a chlorine atom or a bromine atom, and (i) when Hal is a chlorine atom, $R_1'$ is an optionally substituted linear alkyl group; an optionally substituted alkenyl group; an optionally substituted alkynyl group; an optionally substituted cycloalkyl group; or an optionally substituted aromatic hydrocarbon group, and $R_2$ is a hydrogen atom or an optionally substituted hydrocarbon atom, in which $R_1'$ and $R_2$ optionally form a ring in cooperation with a nitrogen atom adjacent thereto, and (ii) when Hal is a bromine atom, $R_1'$ and $R_2$ are each a hydrogen atom or an optionally substituted hydrocarbon group, in which $R_1'$ and $R_2$ optionally form a ring in cooperation with a nitrogen atom adjacent thereto.

[61] A method of controlling noxious organisms as disclosed in [60] wherein the compound is a compound disclosed in any one of [1] through [38].

[62] Use of a compound for preparing a composition for controlling noxious organisms, the compound represented by the general formula:

$$Hal—C≡C—CO—NR_1'R_2 \tag{I'}$$

wherein Hal is a chlorine atom or a bromine atom, and (i) when Hal is a chlorine atom, $R_1'$ is an optionally substituted linear alkyl group; an optionally substituted alkenyl group; an optionally substituted alkynyl group; an optionally substituted cycloalkyl group; or an optionally substituted aromatic hydrocarbon group, and $R_2$ is a hydrogen atom or an optionally substituted hydrocarbon atom, in which $R_1'$ and $R_2$ optionally form a ring in cooperation with a nitrogen atom adjacent thereto, and (ii) when Hal is a bromine atom, $R_1'$ and $R_2$ are each a hydrogen atom or an optionally substituted hydrocarbon group, in which $R_1'$ and $R_2$ optionally form a ring in cooperation with a nitrogen atom adjacent thereto.

[63] Use as disclosed in [62] wherein the compound is a compound disclosed in any one of [1] through [38].

Preferably, there are provided following inventions [64] through [69].

[64] An antifungal composition that destroys or prevents the growth of yeast which comprises the compound disclosed in [2] wherein $R_3$ is a methyl group, a n-butyl group, a n-pentyl group, a n-hexyl group, a n-heptyl group, a n-octyl group, a n-nonyl group, or a n-decyl group, and $R_4$ is a hydrogen atom (corresponding to compounds in Examples 1 through 7 and 10 below).

[65] An antifungal composition that destroys or prevents the growth of one or more fungi selected from the group consisting of Asp., Pen., Cla., Aur., Cha., Tri., and Pae, which comprises the compound disclosed in [2] wherein $R_3$ is a hydrogen atom or a linear $C_{1-10}$ alkyl, and $R_4$ is a hydrogen atom (corresponding to compounds in Examples 1 through 10 below).

[66] An antifungal composition that destroys or prevents the growth of wood rot fungi, which comprises the compound disclosed in [2] wherein $R_3$ is a hydrogen atom or a linear $C_{1-10}$ alkyl group, and $R_4$ is a hydrogen atom (corresponding to compounds in Examples 1 through 10 below).

[67] An antifungal composition that destroys or prevents the growth of yeast, which comprises the compound disclosed in [22] wherein $R_5$ is a hydrogen atom, a n-pentyl group, a n-hexyl group, a n-heptyl group, or a n-octyl group, and $R_6$ is a hydrogen atom (corresponding to compounds in Examples 24 through 26, 29, and 34).

[68] An antifungal composition that destroys or prevents the growth of one or more fungi selected from the group consisting of Asp., Pen., Cla., Aur., Cha., Tri., and Pae, which comprises the compound disclosed in [22] wherein $R_5$ is a hydrogen atom or a linear $C_{1-8}$ alkyl group, and $R_6$ is a hydrogen atom (corresponding to compounds in Examples 24 through 26, 29 through 34).

[69] An antifungal composition that destroys or prevents the growth of wood rot fungi which comprises the compound disclosed in [22] wherein $R_5$ is a hydrogen atom or a linear $C_{1-10}$ alkyl group, and $R_6$ is a hydrogen atom (corresponding to compounds in Examples 24 through 34 below).

DETAILED DESCRIPTION OF THE INVENTION

In the following description, the certain general formulas are used;

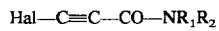

$$\text{Hal—C} \equiv \text{C—CO—NR}_1\text{R}_2 \quad \text{(I)}$$

wherein Hal is a chlorine atom or a bromine atom, and (i) when Hal is a chlorine atom, $R_1$ is a linear alkyl group optionally substituted by 1 through 4 substituents selected from the group consisting of (1) $C_{3-8}$ cycloalkyl, (2) halogen selected from the group consisting of fluorine, chlorine, and iodine, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, (12) $C_{1-4}$ alkanoyl, and (13) five- to ten-membered aromatic heterocyclic group containing, other than the carbon atom(s), 1 through 4 hetero atoms selected from the group consisting of a nitrogen atom, an oxygen atom and a-sulfur atom, the five- to ten-membered aromatic heterocyclic group being optionally substituted by $C_{1-4}$ alkyl, $C_{3-8}$ cycloalkyl, halogen, cyano, hydroxyl, $C_{1-4}$ alkoxy, carboxyl, $C_{1-4}$ alkoxycarbonyl, nitro, amino, carbamoyl, or $C_{1-4}$ alkanoyl; an optionally substituted alkenyl group; an optionally substituted alkynyl group; an optionally substituted cycloalkyl group; or an optionally substituted aromatic hydrocarbon group, and $R_2$ is a hydrogen atom or an optionally substituted hydrocarbon atom, in which $R_1$ and $R_2$ optionally form a ring in cooperation with a nitrogen atom adjacent thereto, and (ii) when Hal is a bromine atom, $R_1$ and $R_2$ are each a hydrogen atom or an optionally substituted hydrocarbon group, in which $R_1$ and $R_2$ optionally form a ring in cooperation with a nitrogen atom adjacent thereto,

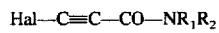

$$\text{Hal—C} \equiv \text{C—CO—NR}_1\text{R}_2 \quad \text{(I')}$$

wherein Hal is a chlorine atom or a bromine atom, a (1) when Hal is a chlorine atom, $R_1'$ is an optionally substituted linear alkyl group; an optionally substituted alkenyl group; and optionally substituted alkynyl group; an optionally substituted cycloalkyl group; or an optionally substituted aromatic hydrocarbon group, and $R_2$ is a hydrogen atom or an optionally substituted hydrocarbon atom, in which $R_1'$ and $R_2$ optionally form a ring in cooperation with a nitrogen atom adjacent thereto, and (ii) when Hal is a bromine atom, $R_1'$ and $R_2$ are each a hydrogen atom or an optionally substituted hydrocarbon group, in which $R_1'$ and $R_2$ optionally form a ring in cooperation with a nitrogen atom adjacent thereto,

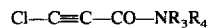

$$\text{Cl—C} \equiv \text{C—CO—NR}_3\text{R}_4 \quad \text{(Ia)}$$

and the compound (Ib) are novel compounds, wherein $R_3$ is a linear alkyl group optionally substituted by 1 through 4 substituents selected from the group consisting of (1) $C_{3-8}$ cycloalkyl, (2) fluorine, chlorine or iodine, (3) cyano, (4) hydroxyl, (5) $C_{1-4}$ alkoxy, (6) carboxyl, (7) $C_{1-7}$ alkoxycarbonyl, (8) ketone, (9) nitro, (10) amino, (11) carbamoyl, (12) $C_{1-4}$ alkanoyl, and (13) five- to ten-membered aromatic heterocyclic group containing, other than the carbon atom(s), 1 through 4 hetero atoms selected from the group consisting of a nitrogen atom, an oxygen atom and a sulfur atom, the five- to ten-membered aromatic heterocyclic group being optionally substituted by $C_{1-4}$ alkyl, $C_{3-8}$ cycloalkyl, halogen, cyano, hydroxyl, $C_{1-4}$ alkoxy, carboxyl, $C_{1-4}$ alkoxycarbonyl, nitro, amino, carbamoyl, or $C_{1-4}$ alkanoyl; an optionally substituted alkenyl group; an optionally substituted alkynyl group; an optionally substituted cycloalkyl group; or an optionally substituted aromatic hydrocarbon group, and $R_4$ is a hydrogen atom or an optionally substituted hydrocarbon atom, in which $R_3$ and $R_4$ optionally form a ring in cooperation with a nitrogen atom adjacent thereto,

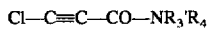

$$\text{Cl—C} \equiv \text{C—CO—NR}_3'\text{R}_4 \quad \text{(Ia')}$$

wherein $R_3'$ is an optionally substituted linear alkyl group, an optionally substituted alkenyl group, an optionally substituted alkynyl group, an optionally substituted cycloalkyl group, or an optionally substituted aromatic hydrocarbon group, and $R_4$ is a hydrogen atom or an optionally substituted hydrocarbon atom, in which $R_3'$ and $R_4$ optionally form a ring in cooperation with a nitrogen atom adjacent thereto, and

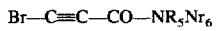

$$\text{Br—C} \equiv \text{C—CO—NR}_5\text{Nr}_6 \quad \text{(Ib)}$$

wherein $R_5$ and $R_6$ are each a hydrogen atom, or an optionally substituted hydrocarbon group, in which $R_5$ and $R_6$ optionally form a ring in cooperation with a nitrogen atom adjacent thereto.

It is preferable that a linear alkyl group, which is represented by $R_1'$ and $R_3'$ and which is optionally substituted, is a linear $C_{1-24}$ alkyl group such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-icosyl, n-docosyl, and n-tetracosyl. In this event, it is preferable that the alkyl group is a linear $C_{1-18}$ alkyl group. It is more preferable that the alkyl group is a linear $C_{1-10}$ alkyl group such as methyl, ethyl, n-propyl, n-butyl, n-pentyl, n-hexyl, n-heptyl, n-octyl, n-nonyl, and n-decyl.

The linear alkyl group is optionally substituted by a substituent. The substituent may be, for example, cycloalkyl (e.g., $C_{3-8}$ cycloalkyl such as cyclopentyl and cyclohexyl), halogen (e.g., fluorine, chlorine, bromine, and iodine), cyano, hydroxyl, $C_{1-4}$ alkoxy (e.g., methoxy, ethoxy, propoxy, and butoxy), carboxyl, $C_{1-4}$ alkoxycarbonyl (e.g., methoxycarbonyl, ethoxycarbonyl, propoxycarbonyl, and butoxycarbonyl), ketone, nitro, amino, carbamoyl, $C_{1-4}$ alkanoyl (e.g., acetyl, propionyl, and butylyl), or an aromatic heterocyclic group (e.g., five- to ten-membered aromatic heterocyclic group containing, other than the carbon atom(s), 1 through 4 hetero atoms selected from the group consisting of a nitrogen atom, an oxygen atom and a sulfur atom, such as 2-furyl, 3-furyl, 2-thienyl, 3-thienyl, 2-pyridyl, 3-pyridyl, 4-pyridyl, thiazolyl, imidazolyl, benzthiazolyl, and benzimidazolyl). The aromatic heterocyclic group is optionally substituted by $C_{1-4}$ alkyl (e.g., methyl, ethyl, propyl, and butyl), cycloalkyl (e.g., $C_{3-8}$ cycloalkyl such as cyclopentyl and cyclohexyl), halogen (e.g., fluorine, chlorine, bromine, and iodine), cyano, hydroxyl, $C_{1-4}$ alkoxy (e.g., methoxy, ethoxy, propoxy, and butoxy), carboxyl, $C_{1-4}$ alkoxycarbonyl (e.g., methoxycarbonyl, ethoxycarbonyl, propoxycarbonyl, and butoxycarbonyl), nitro, amino, carbamoyl, and $C_{1-4}$ alkanoyl (e.g., acetyl, propionyl, and butylyl). Of these substituents for linear alkyl, it is preferable to use five- to ten-membered aromatic heterocyclic group, such as 2-furyl, 3-furyl, 2-thienyl, 3-thienyl, 2-pyridyl, 3-pyridyl, 4-pyridyl, thiazolyl, imidazolyl, benzthiazolyl, and benzimidazolyl, which contains, other than the carbon atom(s), 1 through 4 hetero atoms selected from the group consisting of a nitrogen atom, an oxygen atom and a sulfur atom. Pyridyl is particularly preferable.

Linear alkyl of the linear alkyl group, which is represented by $R_1$ and $R_3$ and is optionally substituted by 1 through 4 substituents selected from the group consisting of (1) $C_{3-8}$ cycloalkyl, (2) halogen selected from the group consisting of fluorine, chlorine, and iodine, (3) cyano, (4) hydroxyl, (5) $C_{1-4}$ alkoxy, (6) carboxyl, (7) $C_{1-4}$ alkoxycarbonyl, (8) ketone, (9) nitro, (10) amino, (11) carbamoyl, (12) $C_{1-4}$ alkanoyl, and (13) five- to ten-membered aromatic heterocyclic group which is optionally substituted by $C_{1-4}$ alkyl, $C_{3-8}$ cycloalkyl, halogen, cyano, hydroxyl, $C_{1-4}$ alkoxy, carboxyl, $C_{1-4}$ alkoxycarbonyl, nitro, amino, carbamoyl, or $C_{1-4}$ alkanoyl and which contains, other than the carbon atom(s), 1 through 4 hetero atoms selected from the group consisting of a nitrogen atom, an oxygen atom and a sulfur atom, may be similar to the linear alkyl represented by $R_1'$ and $R3'$. In addition, specific examples of substituents (1) through (13) may be similar to the substituents for the linear alkyl represented by $R_1'$ and $R_3'$ other than bromine. In other words, $R_1'$ and $R_3'$ do not involve "a linear alkyl group substituted by bromine".

The optionally substituted alkenyl group represented by $R_1'$, $R_3'$, $R_1$ and $R_3$ may be for example, a linear or branched $C_{2-24}$ alkenyl group. Specific examples of such alkenyl include vinyl, 1-propenyl, 2-propenyl, 1-butenyl, 2-butenyl, 3-butenyl, pentenyl, octenyl, and 1,3-butadienyl. In particular, it is preferable to use a linear or branched $C_{2-10}$ alkenyl group.

The alkenyl group is optionally substituted by a substituent. The substituent may be, for example, cycloalkyl (e.g., $C_{3-8}$ cycloalkyl such as cyclopentyl and cyclohexyl), halogen (e.g., fluorine, chlorine, bromine, and iodine), cyano, hydroxyl, $C_{1-4}$ alkoxy (e.g., methoxy, ethoxy, propoxy, and butoxy), carboxyl, $C_{1-4}$ alkoxycarbonyl (e.g., methoxycarbonyl, ethoxycarbonyl, propoxycarbonyl, and butoxycarbonyl), ketone, nitro, amino, carbamoyl, and $C_{1-4}$ alkanoyl (e.g., acetyl, propionyl, and butylyl). Of these substituents for the alkenyl group, halogen (e.g., fluorine, chlorine, bromine, and iodine) is preferably used.

The optionally substituted alkynyl group represented by $R_1'$, $R_3'$, $R_1$, and $R_3$ may preferably be a linear or branched $C_{2-24}$ alkynyl group. Specific examples of such alkynyl group include ethynyl, 1-propynyl, 2-propynyl, 1-butynyl, 2-butynyl, 3-butynyl, pentynyl, octynyl, and decynyl. Of these, it is preferable to use a linear or branched $C_{2-10}$ alkynyl group.

The alkynyl group is optionally substituted by a substituent. Examples of the substituent include cycloalkyl (e.g., $C_{3-8}$ cycloalkyl such as cyclopentyl and cyclohexyl), halogen (e.g., fluorine, chlorine, bromine, and iodine), cyano, hydroxyl, $C_{1-4}$ alkoxy (e.g., methoxy, ethoxy, propoxy, and butoxy), carboxyl, $C_{1-4}$ alkoxycarbonyl (e.g., methoxycarbonyl, ethoxycarbonyl, propoxycarbonyl, and butoxycarbonyl), ketone, nitro, amino, carbamoyl, and $C_{1-4}$ alkanoyl (e.g., acetyl, propionyl, and butylyl). Of these substituents for the alkynyl group, halogen (e.g., fluorine, chlorine, bromine, and iodine) is preferably used.

The optionally substituted cycloalkyl group represented $R_1'$, $R_3'$, $R_1$ and $R_3$ may preferably be a $C_{3-8}$ cycloalkyl group. Specific examples of such cycloalkyl group include monocyclic $C_{3-8}$ cycloalkyl groups such as cyclopropyl, cyclobutyl, cyclopentyl, cyclohexyl, cycloheptyl, and cyclooctyl. It is more preferable to use a $C_{5-7}$ cycloalkyl group (e.g., cyclopentyl, cyclohexyl, and cycloheptyl).

The cycloalkyl group is optionally substituted by a substituent. Examples of the substituent include $C_{1-4}$ alkyl (e.g., methyl, ethyl, propyl, butyl), halogen (e.g., fluorine, chlorine, bromine, and iodine), cyano, hydroxyl, $C_{1-4}$ alkoxy (e.g., methoxy, ethoxy, propoxy, and butoxy), carboxyl, $C_{1-4}$ alkoxycarbonyl (e.g., methoxycarbonyl, ethoxycarbonyl, propoxycarbonyl, and butoxycarbonyl), ketone, nitro, amino, carbamoyl, and $C_{1-4}$ alkanoyl (e.g., acetyl, propionyl, and butylyl). Of these substituents for the cycloalkyl group, $C_{1-4}$ alkyl (e.g., methyl, ethyl, propyl, and butyl) and halogen (e.g., fluorine, chlorine, bromine, and iodine) are preferable.

The optionally substituted aromatic hydrocarbon group represented by $R_1'$, $R_3'$, $R_1$ and $R_3$ may be, for example, an optionally substituted aryl group and an optionally substituted aralkyl group. The optionally substituted aryl group may preferably be mono- through tricyclic aromatic hydrocarbon group, i.e., a $C_{6-18}$ aromatic hydrocarbon group (e.g., $C_{6-18}$ aryl group). Examples of such aromatic hydrocarbons include unsubstituted or substituted phenyl or naphthyl. Unsubstituted or substituted phenyl is particularly preferable.

A substituent for such aryl group may be, for example, a $C_{1-4}$ alkyl group (e.g., methyl, ethyl, propyl, and butyl, which are each optionally substituted further by halogen such as fluorine, chlorine, bromine, and iodine), cycloalkyl (e.g., $C_{3-8}$ cycloalkyl such as cyclopentyl and cyclohexyl), halogen (e.g., fluorine, chlorine, bromine, and iodine), cyano, hydroxyl, $C_{1-4}$ alkoxy (e.g., methoxy, ethoxy, propoxy, and butoxy), carboxyl, $C_{1-4}$ alkoxycarbonyl (e.g., methoxycarbonyl, ethoxycarbonyl, propoxycarbonyl, and butoxycarbonyl), nitro, amino, carbamoyl, $C_{1-4}$ alkanoyl (e.g., acetyl, propionyl, and butylyl). More preferable substituents for the aryl group include, for example, halogen, nitro, and a halogen-substituted $C_{1-4}$ alkyi group (e.g., trifluoromethyl). Specific examples of the substituted aryl group include 2-fluorophenyl, 3-fluorophenyl, 4-fluorophenyl, 2-chlorophenyl, 3-chlorophenyl, 4-chlorophenyl, 3-bromophenyl, 2,4-difluorophenyl, 2,4-dichlorophenyl, 2,4-dibromophenyl, 2-trifluoromethylphenyl, 3-trifluoromethylphenyl, and 4-trifluoromethylphenyl. Of these, a phenyl group substituted by chlorine, fluorine, nitro, or trifluoromethyl (e.g., 3-fluorophenyl, 4-fluorophenyl, 3-chlorophenyl, 4-chlorophenyl, 2,4-dichlorophenyl, 3-nitrophenyl, 4-nitrophenyl, 3-trifluoromethylphenyl, and 4-trifluoromethylphenyl) is more preferable.

The optionally substituted aralkyl group may preferably be an alkyl group substituted by mono through tricyclic aromatic hydrocarbon group. An $C_{1-24}$ alkyl group substituted by a $C_{6-18}$ aryl group is more preferable. Specific examples of such aralkyl group include benzyl, 2-phenylethyl, 1-phenylethyl, 3-phenylpropyl, 4-phenylbutyl, 1-naphtylmethyl, and 2-naphtylmethyl. In particular, a $C_{1-4}$ alkyl group substituted by phenyl (e.g., benzyl, 2-phenylethyl, 1-phenylethyl, and 3-phenylpropyl).

The aralkyl group is optionally substituted by a substituent. Examples of the substituent include $C_{1-4}$ alkyl, (e.g., methyl, ethyl, propyl, and butyl, which are each optionally substituted further by halogen such as fluorine, chlorine, bromine, and iodine), cycloalkyl (e.g., $C_{3-8}$ cycloalkyl such as cyclopentyl and cyclohexyl), halogen (e.g., fluorine, chlorine, bromine, and iodine), cyano, hydroxyl, $C_{1-4}$ alkoxy (e.g., methoxy, ethoxy, propoxy, and butoxy), carboxyl, $C_{1-4}$ alkoxycarbonyl (e.g., methoxycarbonyl, ethoxycarbonyl, propoxycarbonyl, and butoxycarbonyl), nitro, amino, carbamoYl, and $C_{1-4}$ alkanoyl (e.g., acetyl, propionyl, and butylyl). The substituent for the aralkyl group may preferably be halogen, nitro, a halogen-substituted $C_{1-4}$ alkyl group (e.g., trifluoromethyl). Specific examples of the substituted aralkyl group include 2-fluorobenzyl, 3-fluorobenzyl, 4-fluorobenzyl, 2-chlorobenzyl, 3-chlorobenzyl, 4-chlorobenzyl, 3-bromobenzyl, 2,4-difluorobenzyl, 2,4-dichlorobenzyl, 2,4-dibromobenzyl, 2-trifluoromethylbenzyl, 3-trifluoromethylbenzyl, and 4-trifluoromethylbenzyl. Of these, a benzyl group substituted by chlorine, fluorine, nitro, or trifluoromethyl (e.g., 3-fluorobenzyl, 4-fluorobenzyl, 3-chlorobenzyl, 4-chlorobenzyl, 2,4-dichlorobenzyl, 3-nitrobenzyl, 4-nitrobenzyl, 3-trifluoromethylbenzyl, and 4-trifluoromethylbenzyl) is more preferable.

The optionally substituted hydrocarbon group represented by $R_1'$, $R_1$, $R_4$, $R_5$, and $R_6$ may be, for example, an alkyl group, a cycloalkyl group, an alkenyl group, an alkynyl group, an aryl group, and an aralkyl group. Of these, the optionally substituted cycloalkyl, alkenyl, alkynyl, aryl, and aralkyl groups may be similar to those described above.

It is preferable that the alkyl group is a linear or branched $C_{1-24}$ alkyl group. Specific examples of such alkyl group include methyl, ethyl, n-propyl, isopropyl, n-butyl, isobutyl, sec-butyl, tert-butyl, n-pentyl, isoamyl, tert-amyl, n-hexyl, isohexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-icosyl, n-docosyl, and n-tetracosyl. It is more preferable that the alkyl group is a linear or branched $C_{1-18}$ alkyl group. Of these, it is most preferable that the alkyl group is the $C_{1-10}$ alkyl group (e.g., methyl, ethyl, n-propyl, isopropyl, n-butyl, isobutyl, sec-butyl, tert-butyl, n-pentyl, isoamyl, tert-amyl, n-hexyl, isohexyl, n-hephyl, n-octyl, n-nonyl, and n-decyl).

The alkyl group is optionally substituted by a substituent. The substituent may be, for example, cycloalkyl (e.g., $C_{3-8}$ cycloalkyl such as cyclopentyl and cyclohexyl), halogen (e.g., fluorine, chlorine, bromine, and iodine), cyano, hydroxyl, $C_{1-4}$ alkoxy (e.g., methoxy, ethoxy, propoxy, and butoxy), carboxyl, $C_{1-4}$ alkoxycarbonyl (e.g., methoxycarbonyl, ethoxycarbonyl, propoxycarbonyl, and butoxycarbonyl), ketone, nitro, amino, carbamoyl, $C_{1-4}$ alkanoyl (e.g., acetyl, propionyl, and butylyl), an aromatic heterocyclic group (e.g., a five- to ten-membered aromatic heterocyclic group containing, other than the carbon atom(s), 1 through 4 hetero atoms selected from the group consisting of a nitrogen atom, an oxygen atom and a sulfur atom, such as 2-furyl, 3-furyl, 2-thienyl, 3-thienyl, 2-pyridyl, 3-pyridyl, 4-pyridyl, thiazolyl, imidazolyl, benzthiazolyl, and benzimidazolyl, which are each optionally substituted by $C_{1-4}$ alkyl (e.g., methyl, ethyl, propyl, and butyl), cycloalkyl (e.g., $C_{3-8}$ cycloalkyl such as cyclopentyl and cyclohexyl), halogen (e.g., fluorine, chlorine, bromine, and iodine), cyano, hydroxyl, $C_{1-4}$ alkoxy (e.g., methoxy, ethoxy, propoxy, and butoxy), carboxyl, $C_{1-4}$ alkoxycarbonyl (e.g., methoxycarbonyl, ethoxycarbonyl, propoxycarbonyl, and buhoxycarbonyl), nitro, amino, carbamoyl, and $C_{1-4}$ alkanoyl (e.g., acetyl, propionyl, and butylyl)). Of these substituents for the alkyl group, it is preferable to use the five- to ten-membered aromatic heterocyclic group containing, other than the carbon atom(s), 1 through 4 hetero atoms selected from the group consisting of a nitrogen atom, an oxygen atom and a sulfur atom, such as 2-furyl, 3-furyl, 2-thienyl, 3-thienyl, 2-pyridyl, 3-pyridyl, 4-pyridyl, thiazolyl, imidazolyl, benzthiazolyl, and benzimidazolyl. Pyridyl is particularly preferable.

When $R_1'$ and $R_2$, $R_3'$ and $R_4$, $R_1$ and $R_2$, $R_3$ and $R_4$, and $R_5$ and $R_6$ form rings in cooperation of a nitrogen atom adjacent thereto, i.e., when nitrogen-containing rings are formed, it is preferable that each one is a five- to eight-membered ring. An atom other than the nitrogen atom forming the ring may be, for example, carbon and/or nitrogen and/or oxygen and/or sulfur. It is preferable that the number of the hetero atoms (nitrogen, oxygen, and sulfur atoms) forming the ring is from one to four in total. The nitrogen-containing ring may be fused with another ring. For example, when $R_1$ and $R_2$ form the nitrogen-containing ring in cooperation with a nitrogen atom, the group —$NR_1R_2$ itself forms an amino group. This cyclic amino group (—$NR_1R_2$) may be, for example, a five- to ten-membered cyclic amino group containing, other than the nitrogen atom, 1 through 4 atoms selected from the group consisting of a carbon atom, a nitrogen atom, an oxygen atom and a sulfur atom. Specific examples of the cyclic amino group of the type described include 1-pyrrolidyl, 1-imidazolyl, piperidino (1-piperidyl), 1-piperazinyl, 3-oxazolidinyl, hexamethylenimino, heptamethylenimino, morpholino (4-morpholinyl), and 1-indolinyl. Of these, 1-piperidyl is preferable. The cyclic amino group is optionally substituted by a substituent. The substituent may be, for example, $C_{1-4}$ alkyl (e.g., methyl, ethyl, propyl, and butyl), cycloalkyl (e.g., $C_{3-8}$ cycloalkyl such as cyclopentyl and cyclohexyl), halogen (e.g., fluorine, chlorine, bromine, and iodine), cyano, hydroxyl, $C_{1-4}$ alkoxy (e.g., methoxy, ethoxy, propoxy, and butoxy), carboxyl, $C_{1-4}$ alkoxycarbonyl (e.g., methoxycarbonyl, ethoxycarbonyl, propoxycarbonyl, and butoxycarbonyl), ketone, nitro, amino, carbamoyl, $C_{1-4}$ alkanoyl (e.g., acetyl, propionyl, and buhylyl), and aryl (e.g., $C_{6-18}$ aryl such as phenyl and naphthyl). Of these substituents, $C_{1-4}$ alkyl (e.g., methyl, ethyl, propyl, and butyl), and halogen (e.g., fluorine, chlorine, bromine, and iodine) are preferable.

Of the compounds (Ia) and (Ia') contained in the above mentioned compounds (I) and (I'), respectively, preferable ones are those wherein (1) $R_3$ ($R_3$) is a linear alkyl group and $R_4$ is a hydrogen atom, (2) $R_3(R_3')$ is a linear alkyl group and $R_4$ is an alkyl group, (3) $R_3$ ($R_3'$) is an optionally substituted aryl group and $R_4$ is a hydrogen atom, (4) $R_3$ ($R_3'$) is an optionally substituted cycloalkyl group and $R_4$ is a hydrogen atom, and (5) $R_3$ ($R_3'$) and $R_4$ form a nitrogen-containing ring in cooperation with a nitrogen atom adjacent thereto.

When (1) $R_3$ ($R_3'$) is a linear alkyl group and $R_4$ is a hydrogen atom, it is preferable that a linear alkyl group is, for example, a linear $C_{1-18}$ alkyl group. In particular, a linear $C_{1-12}$ alkyl group (e.g., methyl, ethyl, n-propyl, n-butyl, n-pentyl, n-hexyl, n-hephyl, n-octyl, n-nonyl, n-decyl, n-undecyl, and n-dodecyl) is preferable- Of these, a linear $C_{1-10}$ alkyl group (e.g., methyl, ethyl, n-propyl, n-butyl, n-pentyl, n-hexyl, n-heptyl, n-octyl, n-nonyl, and n-decyl) is most preferable.

When (2) $R_3$ ($R_3'$) is a linear alkyl group and $R_4$ is an alkyl group, it is preferable that a linear alkyl group $R_3$ ($R_3'$) is, for example, a linear $C_{1-18}$ alkyl group. In particular, it is preferable that the linear $C_{1-12}$ alkyl group (e.g., methyl, ethyl, n-propyl, n-butyl, n-pentyl, n-hexyl, n-heptyl, n-octyl, n-nonyl, n-decyl, n-undecyl, and n-dodecyl). Of these, a linear $C_{1-10}$ alkyl group, methyl, ethyl, n-propyl, n-butyl, n-pentyl, n-hexyl, n-heptyl, n-octyl, n-nonyl, and n-decyl) are more preferable. A linear $C_{1-6}$ alkyl group (e.g., methyl, ethyl, n-propyl, n-butyl, n-pentyl, and n-hexyl) is most preferable. In addition, it is preferable that the alkyl group of $R_4$ is a linear or branched $C_{1-18}$ alkyl group. In particular, it is preferable that the alkyl group is a linear or branched $C_{1-12}$ alkyl group carbon atoms (e.g., methyl, ethyl, n-propyl, isopropyl, n-butyl, isobutyl, sec-butyl, tert-butyl, n-pentyl, isoamyl, tert-amyl, n-hexyl, isohexyl, n-heptyl, n-octyl, n-nonyl, n-decyl, n-undecyl, and n-dodecyl). Of these, a linear $C_{1-10}$ or branched alkyl group (e.g., methyl, ethyl, n-propyl, isopropyl, n-butyl, isobutyl, sec-butyl, tert-butyl, n-pentyl, isoamyl, tert-amyl, n-hexyl, isohexyl, n-heptyl, n-octyl, n-nonyl, and n-decyl) is more preferable. A linear or branched $C_{1-6}$ alkyl group (e.g., mekhyl, ethyl, n-propyl, isopropyl, n-butyl, isobutyl, sec-butyl, tert-butyl, n-pentyl, isoamyl, tert-amyl, n-hexyl, and isohexyl) is most preferable.

In particular, it is preferable to use a combination of $R_3$ ($R_3'$) of a linear $C_{1-6}$ alkyl group and $R_4$ of a linear or branched $C_{1-6}$ alkyl group.

When (3) $R_3$ ($R_3'$) is an optionally substituted aryl group and $R_4$ is a hydrogen atom, it is preferable that the optionally substituted aryl group of $R_3$ ($R_3'$) is an optionally substituted phenyl group. In particular, an unsubstituted phenyl group and a phenyl group substituted by halogen (e.g., fluorine, chlorine, bromine, and iodine), a trifluoromethyl group, or a nitro group are preferable. Examples of the halogen-substituted phenyl group include 2-fluorophenyl, 3-fluorophenyl, 4-fluorophenyl, 2-chlorophenyl, 3-chlorophenyl, 4-chlorophenyl, and 3-bromophenyl.

When (4) $R_3$ ($R_3'$) is an optionally substituted cycloalkyl group and $R_4$ is a hydrogen atom, the optionally substituted cycloalkyl group of $R_3$ ($R_3'$) may preferably be a $C_{3-8}$ cycloalkyl group (e.g., cyclopropyl, cyclobutyl, cyclopentyl, cyclohexyl, cycloheptyl, and cyclooctyl). Cyclohexyl is particularly preferable.

When (5) $R_3$ ($R_3'$) and $R_4$ form a nitro-gencontaining ring in cooperation with a nitrogen atom adjacent thereto, the nitrogen-containing ring may preferably be a five- to eight-membered nitrogen-containing ring or fused ring of the nitrogen-containing ring and another ring, which contains, other than the nitrogen atom, 1 through 4 hereto atoms such as a carbon atom and/or a nitrogen atom and/or an oxygen atom and/or a sulfur atom as a ring-forming atom or atoms. Specific examples of the cyclic amino group represented by —NR3($R_3'$)$R_4$ when $R_3$ ($R_3'$) and $R_4$ form a nitrogen-containing ring in cooperation with a nitrogen atom adjacent thereto include 1-pyrrolidyl, 1-imidazolyl, piperidino (1-piperidyl), 1-piperazinyl, 3-oxazolidinyl, hexamethylenimino, heptamethylenimino, morpholino (4-morpholinyl), and 1-indolinyl. Of these, 1-piperidyl is most preferable.

Of the compounds (Ib) contained in the above mentioned compounds (I) and (I'), preferable ones are those wherein (1) $R_5$ is a hydrogen atom and $R_6$ is a hydrogen atom, (2) $R_5$ is a linear alkyl group and $R_6$ is a hydrogen atom, (3) $R_5$ is a substituted linear alkyl group and $R_6$ is a hydrogen atom, (4) $R_5$ is an alkyl group and $R_6$ is an alkyl group, (5) $R_5$ is an optionally substituted aryl group and $R_6$ is a hydrogen atom, (6) $R_5$ is an optionally substituted cycloalkyl group and $R_6$ is a hydrogen atom, and (7) $R_5$ and $R_6$ form a nitrogen-containing ring in cooperation with a nitrogen atom adjacent thereto.

When (2) $R_5$ is a linear alkyl group and $R_6$ is a hydrogen atom, it is preferable that the linear alkyl group is the $C_{1-18}$ alkyl group. In particular, a linear $C_{1-12}$ alkyl group (e.g., methyl, ethyl, n-propyl, n-butyl, n-pentyl, n-hexyl, n-heptyl, n-octyl, n-nonyl, n-decyl, n-undecyl, and n-dodecyl) is more preferable. Of these, $C_{1-10}$ alkyl group (e.g., methyl, ethyl, n-propyl, n-butyl, n-pentyl, n-hexyl, n-heptyl, n-octal, n-nonyl, and n-decyl) is most preferable.

When (3) $R_5$ is a substituted linear alkyl group and $R_6$ is a hydrogen atom, it is preferable that the linear $C_{1-18}$ alkyl group. In particular, a linear $C_{1-12}$ alkyl group (e.g., methyl, ethyl, n-propyl, n-butyl, n-pentyl, n-hexyl, n-heptyl, n-octyl, n-nonyl, n-decyl, n-undecyl, and n-dodecyl) is more preferable. Of these, $C_{1-10}$ alkyl group (e.g., methyl, ethyl, n-propyl, n-butyl, n-pentyl, n-hexyl, n-heptyl, n-octyl, n-nonyl, and n-decyl) is most preferable. A substituent for the linear alkyl group may preferably be an aromatic heterocyclic group. More preferably, the substituent may be a five- to ten-membered aromatic heterocyclic group containing, other than the carbon atom, 1 through 4 nitrogen atom(s) and/or oxygen atom(s) and/or sulfur atom(s) as ring-forming atoms. Specific examples of the substituent include 2-furyl, 3-furyl, 2-thienyl, 3-thienyl, 2-pyridyl, 3-pyridyl, 4-pyridyl, thiazolyl, imidazolyl, benzthiazolyl, and benzimidazolyl. Of these, pyridyl is preferable.

When (4) $R_5$ is an alkyl group and $R_6$ is an alkyl group, the alkyl group of $R_5$ may preferably be a linear or branched $C_{1-18}$ alkyl group. For example, preferable alkyl group may be methyl, ethyl, n-propyl, isopropyl, n-butyl, isobutyl, sec-butyl, tert-butyl, n-pentyl, isoamyl, tert-amyl, n-hexyl, isohexyl, n-heptyl, n-octyl, n-nonyl, n-decyl, n-undecyl, n-dodecyl, n-tridecyl, n-tetradecyl, n-pentadecyl, n-hexadecyl, n-heptadecyl, and n-octadecyl. In particular, a linear or branched C1-12 alkyl group (e.g., methyl, ethyl, n-propyl, isopropyl, n-butyl, isobutyl, sec-butyl, tert-butyl, n-pentyl, isoamyl, tert-amyl, n-hexyl, isohexyl, n-heptyl, n-octyl, n-nonyl, n-decyl, n-undecyl, and n-dodecyl) is preferable. Of these, $C_{1-10}$ alkyl group (e.g., methyl, ethyl, n-propyl, isopropyl, n-butyl, isobutyl, sec-butyl, tert-butyl, n-pentyl, isoamyl, tert-amyl, n-hexyl, isohexyl, n-hepkyl, n-octyl, n-nonyl, and n-decyl) is more preferable. $C_{1-6}$ alkyl group (e.g., methyl, ethyl, n-propyl, isopropyl, n-butyl, isobutyl, sec-butyl, tert-butyl, n-pentyl, isoamyl, tert-amyl, n-hexyl, and isohexyl) is most preferable.

$R_6$ may preferably be a linear or branched $C_{1-18}$ alkyl group as in $R_5$. For example, preferable alkyl group may be methyl, ethyl, n-propyl, isopropyl, n-butyl, isobutyl, sec-butyl, tert-butyl, n-pentyl, isoamyl, tert-amyl, n-hexyl, isohexyl, n-heptyl, n-octyl, n-nonyl, n-decyl, n-undecyl, n-dodecyl, n-tridecyl, n-tetradecyl, n-pentadecyl, n-hexadecyl, n-heptadecyl, and n-octadecyl. In particular, a linear or branched $C_{1-12}$ alkyl group (e.g., methyl, ethyl, n-propyl, isopropyl, n-butyl, isobutyl, sec-butyl, tert-butyl, n-pentyl, isoamyl, tert-amyl, n-hexyl, isohexyl, n-heptyl, n-octyl, n-nonyl, n-decyl, n-undecyl, and n-dodecyl) is preferable. Of these, $C_{1-10}$ alkyl group (e.g., methyl, ethyl, n-propyl, isopropyl, n-butyl, isobutyl, sec-butyl, tert-butyl, n-pentyl, isoamyl, tert-amyl, n-hexyl, isohexyl, n-heptyl, n-octyl, n-nonyl, and n-decyl) is more preferable. $C_{1-6}$ alkyl group (e.g., methyl, ethyl, n-propyl, isopropyl, n-butyl, isobutyl, sec-butyl, tert-butyl, n-pentyl, isoamyl, tert-amyl, n-hexyl, and isohexyl) is most preferable.

In particular, it is preferable to use a combination of a $C_{1-6}$ alkyl group as $R_5$ and a $C_{1-6}$ alkyl group as $R_6$.

When (5) $R_5$ is an optionally substituted aryl group and $R_6$ is a hydrogen atom, the optionally substituted aryl group of $R_5$ may preferably be an optionally substituted phenyl group. In particular, an unsubstituted phenyl group and a phenyl group substituted by halogen (e.g., fluorine, chlorine, bromine, and iodine), a trifluoromethyl group, or a nitro group are preferable. Examples of the halogen-substituted phenyl group include 2-fluorophenyl, 3-fluorophenyl, 4-fluorophenyl, 2-chlorophenyl, 3-chlorophenyl, 4-chlorophenyl, and 3-bromophenyl.

When (6) $R_5$ is an optionally substituted cycloalkyl group and $R_6$ is a hydrogen atom, the optionally substituted cycloalkyl of $R_5$ may preferably be a $C_{3-8}$ cycloalkyl group (e.g., cyclopropyl, cyclobutyl, cyclopentyl, cyclohexyl, cycloheptyl, and cyclooctyl). Cyclohexyl is particularly preferable.

When (7) $R_5$ and $R_6$ form a nitrogen-containing ring in cooperation with a nitrogen atom adjacent thereto, the nitrogen-containing ring may preferably be a five- to eight-membered nitrogen-containing ring or fused ring of the nitrogen-containing ring and another ring, which contains, other than the nitrogen atom, 1 through 4 hetero atoms such as a carbon atom and/or a nitrogen atom and/or an oxygen atom and/or a sulfur atom as a ring-forming atom or atoms. Specific examples of the cyclic amino group represented by —NR$_5$R$_6$ when R$_5$ and R$_6$ form a nitrogen-containing ring in cooperation with a nitrogen atom adjacent thereto include 1-pyrrolidyl, 1-imidazolyl, piperidino (1-piperidyl), 1-piperazinyl, 3-oxazolidinyl, hexamethylenimino, heptamethylenimino, morpholino (4-morpholinyl), and 1-indolinyl. Of these, 1-piperidyl is most preferable.

Features of the compound (Ia) according to the present invention are described below.

(1) A compound in which R$_3$ is a linear C$_{1-10}$ alkyl group and R$_4$ is a hydrogen atom (in particular, a compound in which R$_3$ is a linear C$_{6-10}$ alkyl group and R$_4$ is a hydrogen atom) exhibits superior antibacterial activities to a gram-positive bacterium (e.g., *Staphylococcus aureus*, and *Bacillus subtilis*).

(2) A compound in which R$_3$ is a methyl group and R$_4$ is a hydrogen atom exhibits superior antibacterial activities to a gram-negative bacterium (e.g., *Pseudomonas aeruginosa*, and *Escherichia coli*). The antibacterial activities of this compound to the gram-negative bacterium are extremely superior to the antibacterial activities of a known iodopropiolamide compound or of a known chloropropiolamide compound. The present compound is high in water solubility and exhibits superior antibacterial activities to gram-negative bacteria contained in industrial water (e.g., resin emulsions, water-soluble coatings, water-soluble pigment paste, spinning oil, cutting oil, perforating oil, paper mill whitewater, starch slurry, and cooling water; especially the paper mill whitewater). Accordingly, the present compound can advantageously be used as an antideterioration for the industrial water.

(3) A compound in which R$_3$ is a linear C$_{1-10}$ alkyl group and R$_4$ is a hydrogen atom (in particular, a compound in which R$_3$ is a hydrogen atom, a n-methyl group, a n-butyl group, a n-pentyl group, a n-hexyl group, a n-heptyl group, a n-octyl group, a n-nonyl group, or a n-decyl group, and R$_4$ is a hydrogen atom) exhibits superior antifungal activities to a yeast (e.g., *Saccharomyces cerevisiae*, and *Candida albicans*).

(4) A compound in which R$_3$ is a linear C$_{1-10}$ alkyl group and R$_4$ is a hydrogen atom exhibits superior antifungal activities to a fungus such as *Aspergillus niger, Penicillium citrinum, Cladosporium cladosporioides, Aureobasidium pullulans, Chaetomium globossum, Trichoderma viride*, and *Paecilomyces variotii*.

(5) A compound in which R$_3$ is a linear C$_{1-10}$ alkyl group and R$_4$ is a hydrogen atom exhibits superior antifungal activities to a wood rot fungus (e.g., *Tyromyces palustris*, and *Coriolus versicolor*).

(6) A compound in which R$_3$ is a phenyl group substituted by chlorine, a trifluoromethyl group or a nitro group and R$_4$ is a hydrogen atom exhibits superior antibacterial and antifungal activities to a gram-positive bacterium (e. g., *Staphylococcus aureus*, and *Bacillus subtilis*), a fungus [a yeast (e.g., *Saccharomyces cerevisiae*, and *Candida albicans*), *Aspergillus niger, Penicillium citrinum, Cladosporium cladosporioides, Aureobasidium pullulans, Chaetomium globossum, Trichoderma viride*, and *Paecilomyces variotii*, and a wood rot fungus (e.g., *Tyromyces palustris*, and *Coriolus versicolor*)].

(7) A compound in which R$_3$ and R$_4$ are each a methyl group, or R$_3$ and R$_4$ form a 1-piperidyl group in cooperation with a nitrogen atom adjacent thereto exhibits superior antibacterial and antifungal activities to a gram-positive bacterium (e.g., *Staphylococcus aureus*, and *Bacillus subtilis*), a fungi [preferably, a fungus other than a yeast (e.g., *Aspergillus niger, Penicillium ci trinum, Cladosporium cladosporioides, Aureobasidium pullulans, Chaetomium globossum, Paecilomyces variotti*, and a wood rot fungus (e.g., *Tyromyces palustris*, and *Coriolus versicolor*))].

Features of the compound (Ib) according to the present invention are described below.

(1) A compound in which R$_5$ is a hydrogen atom or a linear C$_{1-10}$ alkyl group and R$_6$ is a hydrogen atom (in particular, a compound in which R$_5$ is a hydrogen atom or a linear C$_{6-10}$ alkyl group and R$_6$ is a hydrogen atom) exhibits superior antibacterial activities to a gram-positive bacterium (e.g., *Staphylococcus aureus*, and *Bacillus subtilis*).

(2) A compound in which R$_5$ is a hydrogen atom or a methyl group and R$_6$ is a hydrogen atom (in particular, a compound in which R$_5$ and R$_6$ are each a hydrogen atom) exhibits superior antibacterial activities to a gram-negative bacterium (e.g., *Pseudomonas aeruginosa*, and *Escherichia coli*). The antibacterial activities of this compound to the gram-negative bacterium are extremely superior to the antibacterial activities of a known iodopropiolamide compound or of a known chloropropiolamide compound. The present compound is high in water solubility and exhibits superior antibacterial activities to gram-negative bacteria contained in industrial water (e.g., resin emulsions, water-soluble coatings, water-soluble pigment paste, spinning oil, cutting oil, perforating oil, paper mill whitewater, starch slurry, and cooling water; especially the paper mill whitewater). Accordingly, the present compound can advantageously be used as an antideterioration for the industrial water.

(3) A compound in which R$_5$ is a hydrogen atom or a linear C$_{1-10}$ alkyl group and R$_6$ is a hydrogen atom (in particular, a compound in which R$_5$ is a hydrogen atom, a n-pentyl group, a n-hexyl group, a n-heptyl group, or a n-octyl group, and R$_6$ is a hydrogen atom) exhibits superior antifungal activities to a yeast (e.g., *Saccharomyces cerevisiae*, and *Candida albicans*).

(4) A compound in which R$_5$ is a hydrogen atom or a linear C$_{1-10}$ alkyl group and R$_6$ is a hydrogen atom (in particular, a compound in which R$_5$ is a hydrogen atom or a linear C$_{1-8}$ alkyl group and R$_6$ is a hydrogen atom) exhibits superior antifungal activities to a fungi such as *Aspergillus niger, Penicillium citrinum, Cladosporium cladosporioides, Aureobasidium pullulans, Chaetomium globossum, Trichoderma viride*, and *Paecilomyces variotti*.

(5) A compound in which R$_5$ is a hydrogen atom or a linear C$_{1-10}$ alkyl group and R$_6$ is a hydrogen atom exhibits superior antifungal activities to a wood rot fungus (e.g., *Tyromyces palustris*, and *Coriolus versicolor*).

(6) A compound in which R$_5$ is a phenyl group substituted by chlorine, a trifluoromethyl group or a nitro group and R$_6$ is a hydrogen atom exhibits superior antibacterial and antifungal activities to a gram-positive bacterium (e.g., *Staphylococcus aureus, and Bacillus subtilis*), a fungus [a yeast (e.g., *Saccharomyces cerevisiae*, and *Candida albicans*), *Aspergillus niger, Penicillium citrinum, Cladosporium cladosporioides, Aureobasidium pullulans, Chaetomium globossum, Trichoderma viride*, and *Paecilomyces variotti*, and a wood rot fungus (e.g., *Tyromyces palustris*, and *Coriolus versicolor*)].

(7) A compound in which R$_5$ and R$_6$ are each a methyl group, or R$_5$ and R$_6$ form a 1-piperidyl group in cooperation with a nitrogen atom adjacent thereto exhibits superior antibacterial and antifungal activities to a gram-positive bacterium (e.g., *Staphylococcus aureus*, and *Bacillus subtilis*), a fungus [preferably, a fungus other than a yeast (e.g., *Aspergillus niger, Penicillium citrinum, Cladosporium cladosporioides, Aureobasidium pullulans, Chaetomium globossum, Paecilomyces variotti*, and a wood rot fungus (e.g., *Tyromyces palustris*, and *Coriolus versicolor*))].

The compound (I') according to the present invention may be produced through any one of following methods [A] through [C].

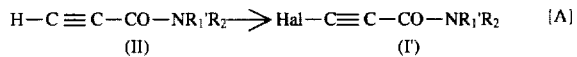

This method is to produced the compound (I') according to the present invention by means of chlorinating or brominating a propiolamide compound (II). More specifically, this method is to prepare the compound (I') by means of dissolving the compound (II) in an organic solvent for a subsequent reaction with a chlorinating agent or a brominating agent. The organic solvent selected is the one that does not react with the chlorinating agent or the brominating agent. The organic solvent of the type described which is used favorably may be, for example, an alcoholic solvent such as methanol, and ethanol, an ether solvent such as ethyl ether, tetrahydrofuran, and dioxane, acetonitrile, acetone, chloroform, dichloromethane, N,N-dimethylformamide (DMF), and dimethylsulfoxide (DMSO). The solvent is preferably anhydrous but a water-containing solvent may sometimes yield good results.

The chlorinating agent used may be, for example, chlorine, N-chlorosuccinimide, sodium hypochlorite, potassium chloride-sodium hypochlorite, cuprous chloride, zinc chloride, carbon tetrachloride-triphenylphosphine, sulfuryl chloride, and trifluoromethanesulfonyl chloride. An adequate amount of the chlorinating agent is in a range from about 1.0 to 1.5 moles per one mole of the compound (II). A base, if used, may enhance the chlorination reaction in many cases. Examples of the base include sodium hydroxide, potassium hydroxide, sodium hydride, sodium amide, potassium carbonate, silver oxide, silver carbonate, tertiary amine (e.g., triethylamine, and pyridine), sodium methoxide, sodium ethoxide, n-butyllithium, and potassium tert-butoxide. The reaction may be accelerated depending on the type of the base with the addition of a phase transfer catalyst such as tetrabutylammonium bromide, tetraoctylammonium bromide, benzyltriethylammonium chloride, octadecyltrimethylammonium chloride, and tetrabutylammonium hydrogen sulfate. The amount of the base used may typically be about 1.0 to 2.5 moles per one mole of the compound (II). The reaction will readily proceed with the addition of a catalytic amount of silver nitrate in place of the base when the chlorinating agent used is N-chlorosuccinimide. The reaction may be performed under a cooled, room, or heated temperature but typically performed at a room temperature.

The reaction time depends on the type of the chlorinating agent and the reaction temperature. However, the reaction time may typically be from 5 minutes to 3 hours. After the reaction, the objective compound (I') can be isolated from the reaction solution by means of a typical purification method such as a combination of, for example, solvent extraction, distillation, column chromatography, liquid chromatography, and recrystallization.

The brominating agent used may be, for example, bromine, N-bromosuccinimide, sodium hypobromite, potassium bromide-sodium hypochlorite, cuprous bromide, zinc bromide, and carbon tetrabromide-triphenylphosphine. The amount of the brominating agent used may suitably be in a range from about 1.0 to 1.5 moles per one mole of the compound (II). A base, if used, may enhance the chlorination reaction in many cases. Examples of the base include sodium hydroxide, potassium hydroxide, sodium hydride, sodium amide, potassium carbonate, silver oxide, silver carbonate, tertiary amine (e.g., triethylamine, and pyridine), sodium methoxide, sodium ethoxide, n-butyllithium, and potassium tert-butoxide. The reaction may be accelerated depending on the type of the base with the addition of a phase transfer catalyst such as tetrabutylammonium bromide, tetraoctylammonium bromide, benzyltriethylammonium chloride, octadecyltrimethylammonium chloride, and tetrabutylammonium hydrogen sulfate. The amount of the base used may typically be about 1.0 to 1.5 moles per one mole of the compound (II). The reaction will readily proceed with the addition of a catalytic amount of silver nitride in place of the base when the brominating agent used is N-bromosuccinimide. The reaction may be performed under a cooled, room, or heated temperature but typically performed at a room temperature.

The reaction time depends on the type of the chlorinating agent and the reaction temperature. However, the reaction time may typically be from 5 minutes to 3 hours. After the reaction, the objective compound (I') can be isolated from the reaction solution by means of a typical purification method such as a combination of, for example, solvent extraction, distillation, column chromatography, liquid chromatography, and recrystallization.

The source compound (II) may be those commercially available, or those prepared through a known method or its equivalence. The known methods of preparing the source compound (II) include, for example, a method of condensing propiolic acid and amine [Japanese J. Pharmacology, Vol. 102, page 278 (1982); Japanese Patent Publication No. 58885/1985; and Japanese J. Syn. Comm., Vol. 23, page 2003, (1993)], a method of reacting propiolylhalide with amine as well as a method of reacting propiolic anhydride with amine (Syn. Comm., Vol. 23, page 2003 (1993)), a method of reacting propiolic acid ester with amine (J. Org. Chem., Vol. 30, page 2660 (1965)), a method using the Ritter reaction between cyano acetylene and alcohol (J. Chem., Soc. (C), page 406 (1969)), and a method of reacting an acetylene derivative with isocyanate (Syn. Comm., Vol. 23, page 2003 (1993)).

Alternatively, the source compound (II) may be obtained by using acrylic amide through the following steps:

$$CH_2 = CH-CO-NR_1'R_2 + X_2 \quad (A)$$

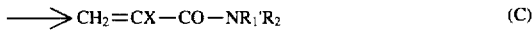

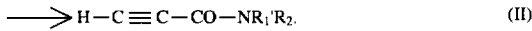

More specifically, halogen such as chlorine, bromine, and iodine is added to acrylic amide (A) to produce a compound (B), which is then dehydrohalogenated to the compound (II) by way of a compound (C). The acrylic amide (A) can readily be prepared through any one of common methods by using acrylic acid, acrylic acid ester, acrylic acid chloride, or acrylonitrile.

Addition of halogen to the acrylic amide (A) is performed by means of reacting an equimolar amount of halogen (chlorine, bromine, iodine) in an organic solvent that does not inhibit the present reaction, such as chloroform, dichloromethane, ethyl ether, dioxane, benzene, and toluene.

Dehydrohalogenation of the compound (B) is achieved by means of dissolving the compound (B) in a solvent to react a base therewith. The compound may be isolated as an intermediate (C) and be reacted with a base to prepare the compound (II). Alternatively, the compound (II) may be prepared in the subsequent single step from the compound (B) without isolating the intermediate (C). The solvent used is not limited specifically. Examples of the solvent include organic solvents such as chloroform, dichloromethane, ethyl ether, dioxane, benzene, toluene, acetonitrile, and petroleum ether; water alone; or mixed solvents of an organic solvent and water. The base used may be, for example, sodium hydroxide, potassium hydroxide, sodium carbonate, potassium carbonate, sodium hydrogencarbonate, potassium hydrogencarbonate, sodium acetate, potassium acetate, ammonium acetate, tertiary amine (e.g., triethylamine, and pyridine), potassium tert-butoxide, sodium hydride, sodium amide, sodium fluoride, potassium fluoride, and a basic anion exchange resin. The reaction may be accelerated with the addition of a phase transfer catalyst such as tetrabutylammonium bromide, tetraoctylammonium bromide, benzyltriethylammonium chloride, octadecyltrimethylammonium chloride, and tetrabutylammonium hydrogen sulfate.

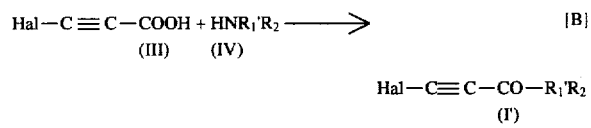

This method is to prepare the compound (I') according to the present invention by means of reacting 3-halopropiolic acid (III, including salts thereof), or acid halide thereof (e.g., chloride, bromide, and iodide) (III') with amine (IV, including salts thereof) to amidate it. When 3-halopropiolic acid or a salt thereof (III) is used, the compound (III) is dissolved in an organic solvent, with which amine or a salt thereof (IV) is reacted to prepare the compound (I'). The salt of 3-halopropiolic acid used may be, for example, a sodium salt, a potassium salt, or an ammonium salt. On the other hand, the salt of amine $HNR_1R_2$ used may be, for example, a salt with an inorganic acid such as hydrochloric acid and sulfine, or a salt with an organic acid such as acetic acid and paratoluene sulfonate. The organic solvent preferably used may be an ether solvent such as ethyl ether, tetrahydrofuran and a halogenated hydrocarbon solvent such as dichloromethane and chloroform. The organic solvent used may be an anhydrous one or a water-containing one. The amount of amine used is preferably in a range from about 1.0 to 1.5 moles, and more preferably in a range from about 1.0 to 1.2 moles per one mole of the compound (III). In many cases, the present amidation reaction may proceed readily with the use of a dehydrating condensation agent such as N,N-dicyclohexylcarbodiimide, diethyl cyanophosphate, and carbonyldiimidazole. The amount of the dehydrating condensation agent used may typically be from about 1.0 to 1.5 moles per one mole of the compound (III). The reaction may be performed at a room temperature or under heat but is typically performed at a temperature between 0° C. and a room temperature. The reaction time is from 1 to 3 hours.

When 3-halopropiol acid halide (III') is used, the compound (III') is dissolved in an organic anhydrous solvent, with which amine (IV, including salts thereof) to prepare the compound (I'). The above mentioned salts may also be used as the salt of the amine $HNR_1R_2$. The organic solvent preferably used may be, for example, a halogenated hydrocarbon solvent such as dichloromethane and chloroform, and an ether solvent such as ethyl ether and tetrahydrofuran. The amount of amine (IV) used is preferably in a range from about 1.0 to 1.5 moles, and more preferably from about 1.0 to 1.2 moles per one mole of the compound (III'). The present amidation reaction may proceed readily with the use of an oxygen scavenger such as pyridine and triethylamine. The amount of the oxygen scavenger used is typically in a range from about 1.0 to 1.5 moles per one mole of the compound (III'). The reaction may be performed under a cooled, room, or heated temperature but is performed typically at a temperature between −10 to 10° C. The reaction time is typically from 1 to 3 hours.

Regardless of whether an acid or a salt thereof or acid halide (III') is used as the compound (III), the objective compound (I') can be isolated from the reaction solution through a combination of solvent extraction, distillation, column chromatography, liquid chromatography, and recrystallization.

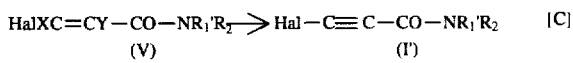

wherein X is Cl or Br and Y is H or X is H and Y is Cl, Br, or I.

This method is to prepare the compound (I') according to the present invention by means of dehydrohalogenation reaction of 3,3-dihalogeno- or 2-halogeno- 3-halogenoacrylamide (V). More specifically, the compound (V) is dissolved in a solvent, with which a base is reacted to prepare the compound (I'). The solvent used is not limited specifically. Examples of the solvent include organic solvents such as methanol, ethanol, acetonitorile, and ethyl acetate; water alone; or mixed solvents of an organic solvent and water. The base used may be, for example, sodium hydroxide, potassium hydroxide, sodium carbonate, potassium carbonate, sodium hydrogencarbonate, potassium hydrogencarbonate, and tertiary amine (e.g., triethylamine, and pyridine). The amount of the base used is typically in a range from about 1.0 to 1.5 moles per one mole of the compound (V). The reaction may be performed under a cooled, room, or heated temperature. The reaction time is typically from 1 to 5 hours. After the reaction, the objective compound (I') can be isolated from the reaction solution through a combination of solvent extraction, distillation, column chromatography, liquid chromatography, and recrystallization. The compound (V) may be the one prepared through a known method (for example, a method disclosed in Japanese J. Pharmacology, Vol. 54, page 25 (1934)) or its equivalent from dihalogenoacrylic acid or an ester thereof.

The present invention has following effects.

The compound (I') according to the present invention inhibits the growth of a wide range of bacteria and fungi, so that compositions containing the present compound can effectively be used as antimicrobial/antifungal composition. In particular, the compound exhibits a strong antimicrobial effects to the bacteria and fungi and can thus be used advantageously against bacterial and fungal damages in various fields including industrial fields. More specifically, the compound may be used as composition for preventing deterioration of industrial products such as plastics, coatings, resins and photographic developing agents, and industrial water. In addition, the compound may be used as a slime controlling agent, and a wood preservative for preventing detrioration of wood.

The compound (I') also has activities of an antifungal agent, an insecticide, an acaricide, and a termiticide, and can thus be used effectively and widely as a composition for controlling noxious organisms. The present compound as it is may be used as the composition for controlling noxious organisms without addition of any other substances. However, the compound may typically be mixed with a carrier and additives and formed into emulsion, a hydration agent, powder, granules, or oil. A solid carrier for the powder may be, for example, talc, clay, or bentonire. The solid carrier for the granules may be, for example, sepiolite, attapulgite, zeolite, natural pumice, or pearlite. Examples of a solvent used for the emulsion or the oil include alcohols (such as ethanol), ketones, glycol ethers, petroleum solvents, aliphatic hydrocarbons, aromatic hydrocarbons (such as benzene), and alkylbenzenes. A dispersing agent to water may be, for example, alkylbenzenesulfonate, higher alcohol sulfonate, polyoxyethylenealkylallylether, and poly(vinyl alcohol). In addition, the compound (I') may be used in a form of a charate compound with a host compound such as a cyclic saccharides (e.g., cyclodextrin) to ensure higher safety. Further, the compound (I') may be mixed with other antimicrobial/antifungal agents, antiseptics, insecticides, and termiticides.

The compound (I') according to the present invention may typically be in the form of oil, though any one of the above mentioned forms is possible, when used as wood preservative. For example, the compound (I') is dissolved in the above mentioned solvent at a concentration of typically from about 0.1% to 10% by weight, preferably from about 0.5% to 5% by weight. The compound is thus prepared as oil with the above mentioned dispersing agent added, if necessary. When the present composition is used as wood preservative, the amount of the present oil preparation required for treating 1 $m^2$ of wood may typically be from 10 to 100 kg, provided that 1% by weight of the present compound (I') be contained.

The compound (I') according to the present invention may typically be in the form of emulsion, hydration agent, powder, or granules, though any one of the above mentioned forms is possible, when used as the antibacterium composition (or a composition for preventing deterioration of industrial water containing the anti-gram-positive bacterium, the gram-negative bacterium and so on). For example, the compound (I') is mixed with the above mentioned carrier at a concentration typically in a range from about 0.1% to 10% by weight, and preferably from about 0.5% to 5% by weight. If necessary, the additives may adequately be added to prepare the emulsion, hydration agent, powder, or granules. In particular, it is preferable to use the compound (I') as the inclusion complex with cyclodextrin. When the industrial water containing the gram-negative bacterium is treated with the present composition, the compound (I') is used typically at an amount of from about 0.002% to 1%, preferably from 0.01% to 0..5% relative to the industrial water. In this event, the present composition may be added to the industrial water either through a continuation process or an intermittent process, which may be determined adequately according to an antimicrobial spectrum and by the economical considerations.

As mentioned above, the compound (I') according to the present invention has the effects of inhibiting the growth of various bacteria and fungi. In addition, the present compound has various favorable properties such as high thermal stability and low fish toxicity, and is difficult to be colored.

The present invention is described more in detail below in the context of a specifically delineated set of Examples. In addition, Test Example 1 is given to illustrate effectiveness of the compound according to the present invention. However, it should be understood that the present invention is not limited to those Examples as long as not being depart from the spirit and scope of the appended claims.

EXAMPLE 1

N-(n-hexyl)-3-chloropropiolamide 2.45 g of N-(n-hexyl)propiolamide was dissolved in 40 ml of dry THF, which was cooled to −78° C. 20 ml of n-butyllithium hexane solution (1.6 mol/l) was added thereto, and the mixture was stirred for 10 minutes. 4.28 g of N-chlorosuccinimide was added thereto, and the resultant mixture was stirred at −78° C. for 2 hours. The mixture was allowed to be warmed to −30° C., to which 10 ml of water was added. The mixture was then stirred overnight at a room temperature. Ethyl acetate and water were added to the reaction solution for separation. An organic phase was concentrated under reduced pressure. A residue was purified by the silica gel column chromatography (eluent: ethyl acetate/hexane=1/9). N-(n-hexyl)-3-chloropropiolamide (2.50 g) was obtained as a colorless oil.

$^1$H-NMR (CDC$_3$): δ0.90 (t, 3H), 1.20–1.45 (m, 6H), 1.45–1.60 (m, 2H), 3.30 (dt, 2H), 5.95 (br, 1H)

Elemental Analysis (%): Calculated for C$_3$H$_{14}$NOCl: C, 57.60; H, 7.52; N, 7.46 Found: C, 57.17; H, 7.56; N, 7.49

EXAMPLE 2

N-(n-heptyl)-3-chloropropiolamide

By a procedure analogous to Example 1, 2.40 g of N-(n-heptyl)-3-chloropropiolamide was obtained as colorless crystals from 2.51 g of N-(n-heptyl)propiolamide.

Melting Point: 42.1°–43.8° C.

$^1$H-NMR (CDCl$_3$): δ0.90 (t, 3H), 1.20–1.45 (m, 8H), 1.45–1.60 (m, 2H), 3.30 (dt, 2H), 5.90 (br, 1H)

Elemental Analysis (%): Calculated for C$_{10}$H$_{16}$NOCl: C, 59.55; H, 8.00; N, 6.94 Found: C, 59.43; H, 7.89; N, 6.83

EXAMPLE 3

N-(n-octyl)-3-chloropropiolamide

By a procedure analogous to Example 1, 2.50 g of N-(n-octyl)-3-chloropropiolamide was obtained as colorless crystals from 2.50 g of N-(n-octyl)propiolamide.

Melting Point: 32.0°–35.8° C.

$^1$H-NMR (CDCl$_3$): δ0.90 (t, 3H), 1.20–1.40 (m, 10H), 1.40–1.60 (m, 2H), 3.30 (dt, 2H), 5.95 (br, 1H)

Elemental Analysis (%): Calculated for C$_{11}$H$_{18}$NOCl: C, 61.25; H, 8.41; N, 6.49 Found: C, 61.26; H, 8.43; N, 6.42

EXAMPLE 4

N-(n-nonyl)-3-chloropropiolamide

By a procedure analogous to Example 1, 2.60 g of N-(n-nonyl)-3-chloropropiolamide was obtained as colorless crystals from 2.34 g of N-(n-nonyl)propiolamide.

Melting Point: 45.7°–47.3° C.

$^1$H-NMR (CDC$_3$): δ0.90 (t, 3H), 1.20–1.40 (m, 12H), 1.40–1.60 (m, 2H), 3.30 (dt, 2H), 5.95 (br, 1H)

Elemental Analysis (%): Calculated for C$_{12}$H$_{20}$NOCl: C, 62.73; H, 8.77; N, 6.10 Found: C, 62.77; H, 9.06; N, 5.98

EXAMPLE 5

N-(n-decyl)-3-chloropropiolamide

By a procedure analogous to Example 1, 2.65 g of N-(n-decyl)-3-chloropropiolamide was obtained as colorless crystals from 2.51 g of N-(n-decyl)propiolamide.

Melting Point: 44.2°–46.9° C.

$^1$H-NMR (CDCl$_3$): δ0.90 (t, 3H), 1.20–1.40 (m, 14H), 1.40–1.60 (m, 2H), 3.30 (dt, 2H), 5.95 (br, 1H)

Elemental Analysis (%): Calculated for $C_{13}H_{22}NOCl$: C, 64.05; H, 9.10; N, 5.75 Found: C, 64.23; H, 9.22; N, 5.70

EXAMPLE 6

N-(n-pentyl)-3-chloropropiolamide

By a procedure analogous to Example 1, 3.16 g of N-(n-pentyl)-3-chloropropiolamide was obtained as a colorless oil from 3.00 g of N-(n-pentyl)propiolamide.

$^1$H-NMR (CDCl$_3$): δ0.90 (t, 3H), 1.20–1.40 (m, 4H), 1.40–1.60 (m, 2H), 3.30 (dt, 2H), 6.00 (br, 1H)

Elemental Analysis (%): Calculated for $C_8H_{12}NOCl$: C, 55.34; H, 6.97; N, 8.07 Found: C, 54.79; H, 7.00; N, 7.92

EXAMPLE 7

N-methyl-3-chloropropiolamide

By a procedure analogous to Example 1, 2.97 g of N-methyl-3-chloropropiolamide was obtained as a colorless oil from 5.00 g of N-methylpropiolamide.

$^1$H-NMR (CDCl$_3$): δ2.88 (d, 3H), 5.94 (br, 1H)

Elemental Analysis (%): Calculated for $C_4H_4NOCl$: C, 40.88; H, 3.43; N, 11.92 Found: C, 40.77; H, 3.37; N, 12.17

EXAMPLE 8

N-ethyl-3-chloropropiolamide

By a procedure analogous to Example 1, 4.17 g of N-ethyl-3-chloropropiolamide was obtained as a colorless oil from 3.50 g of N-ethylpropiolamide.

$^1$H-NMR (CDCl$_3$): δ1.18 (t, 3H), 3.27–3.50 (m, 2H), 7.15 (br, 1H)

Elemental Ana lysis (%): Calculated for $C_5H_6NOCl$: C, 45.65; H, 4.60; N, 10.65 Found: C, 45.89; H, 4.69; N, 10.89

EXAMPLE 9

N-propyl-3-chloropropiolamide

By a procedure analogous to Example 1, 4.57 g of N-propyl-3-chloropropiolamide was obtained as a colorless oil from 3.50 g of N-propylpropiolamide.

$^1$H-NMR (CDCl$_3$): δ0.97 (t, 3H), 1.48–1.67 (m, 2H), 3.28 (dt, 2H), 6.11 (br, 1H)

Elemental Analysis (%): Calculated for $C_6H_8NOCl$: C, 49.50; H, 5.54; N, 9.62 Found: C, 49.28; H, 5.75; N, 9.62

EXAMPLE 10

N-butyl-3-chloropropiolamide

By a procedure analogous to Example 1, 3.18 g of N-butyl-3-chloropropiolamide was obtained as a colorless oil from 3.00 g of N-butylpropiolamide.

$^1$H-NMR (CDCl$_3$): δ0.93 (t, 3H), 1.25–1.60 (m, 4H), 3.30 (dt, 2H), 6.25 (br, 1H)

Elemental Analysis (%): Calculated for $C_7H_{10}NOCl$: C, 52.67; H, 6.31; N, 8.78; Cl, 22.21 Found: C, 52.08; H, 6.13; N, 8.40; Cl, 21.79

EXAMPLE 11

N-dodecyl-3-chloropropiolamide

By a procedure analogous to Example 1, 3.72 g of N-dodecyl-3-chloropropiolamide was obtained as colorless crystals from 5.00 g of N-dodecylpropiolamide.

Melting Point: 53.5°–54.5° C.

$^1$H-NMR (CDCl$_3$): δ0.88 (t, 3H), 1.28 (br, 18H), 1.51 (t, 2H), 3.30 (dt, 2H), 5.82 (br, 1H)

Elemental Analysis (%): Calculated for $C_{13}H_{26}NOCl$: C, 66.28; H, 9.46; N, 5.15 Found: C, 66.33; H, 9.68; N, 5.38

EXAMPLE 12

N-tetradecyl-3-chloropropiolamide

By a procedure analogous to Example 1, 4.29 g of N-tetradecyl-3-chloropropiolamide was obtained as colorless crystals from 5.00 g of N-tetradecylpropiolamide.

Melting Point: 59.5°–60.5° C.

$^1$H-NMR (CDCl$_3$): δ0.89 (t, 3H), 1.29 (br, 22H), 1.5 (t, 2H), 3.29 (dt, 2H), 6.0 (br, 1H)

Elemental Analysis (%): Calculated for $C_{17}H_{30}NOCl$: C, 68.09; H, 10.08; N, 4.67 Found: C, 67.96; H, 9.83; N, 4.77

EXAMPLE 13

N-octadecyl-3-chloropropiolamide

By a procedure analogous to Example 1, 1.59 g of N-octadecyl-3-chloropropiolamide was obtained as colorless crystals from 5.00 g of N-octadecylpropiolamide.

Melting Point: 63.0°–64.5° C.

$^1$H-NMR (CDCl$_3$): δ0.89 (t, 2H), 1.29 (br, 30H), 1.50 (t, 2H), 3.29 (dt, 2H), 5.79 (br, 1H)

Elemental Analysis (%): Calculated for $C_{21}H_{38}NOCl$: C, 70.85; H, 10.76; N, 3.93 Found: C, 70.73; H, 10.95; N, 4.02

EXAMPLE 14

N-(m-chlorophenyl)-3-chloropropiolamide

By a procedure analogous to Example 1, 0.69 g of N-(m-Chlorophenyl)-3-chloropropiolamide was obtained as colorless crystals from 0.72 g of N-(m-chlorophenyl)propiolamide.

Melting Point: 134.6°–134.9° C.

$^1$H-NMR (CDCl$_3$): δ7.11–7.37 (m, 4H), 7.6 (br, 1H)

Elemental Analysis (%): Calculated for $C_9H_5NOCl_2$: C, 50.50; H, 2.35; N, 6.54 Found: C, 50.34; H, 2.28; N, 6.41

EXAMPLE 15

N-(p-chlorophenyl)-3-chloropropiolamide

By a procedure analogous to Example 1, 0.44 g of N-(p-chlorophenyl)-3-chloropropiolamide as brown crystals from 0.72 g of N-(p-chlorophenyl)propiolamide.

Melting Point: 169.3°–169.5° C.

¹H-NMR (CDCl₃): δ7.30 (d, 2H), 7.46 (d, 2H), 7.5 (br, 1H)

Elemental Analysis (%): Calculated for $C_3H_3NOCl_2$: C, 50.50; H, 2.35; N, 6.54 Found: C, 50.42; H, 2.36; N, 6.24

EXAMPLE 16

N-(m-trifluoromethylphenyl)-3-chloropropiolamide

By a procedure analogous to Example 1, 0.25 g of N-(m-trifluoromethylphenyl)-3-chloropropiolamide as yellow oil from 0.85 g of N-(m-trifluoromethylphenyl)propiolamide.

¹H-NMR (CDCl₃): δ7.39–7.51 (m, 2H), 7.71–7.78 (m, 3H)

Elemental Analysis (%): Calculated for $C_{10}H_5NOClF_3$: C, 48.51; H, 2.04; N, 5.66 Found: C, 48.03; H, 2.10; N, 5.16

EXAMPLE 17

N-(m-nitrophenyl)-3-chloropropiolamide

By a procedure analogous to Example 1, 0.18 g of N-(m-nitrophenyl)-3-chloropropiolamide as brown solid from 0.76 g of N-(m-nitrophenyl)propiolamide.

Melting Point: 136.0°–137.0° C.

¹H-NMR (CDCl₃): δ7.53 (t, 1H), 7.7 (br, 1H), 7.91–8.05 (m, 2H), 8.36 (t, 1H)

Elemental Analysis (%): Calculated for $C_9H_3N_2O_3Cl$: C, 48.13; H, 2.24; N, 2.47 Found: C, 48.97; H, 2.81; N, 11.86

EXAMPLE 18

N-(2,4-dichlorophenyl)-3-chloropropiolamide

By a procedure analogous to Example 1, 0.47 g of N-(2,4-dichlorophenyl)-3-chloropropiolamide was obtained as colorless crystals from 0.86 g of N-(2,4-dichlorophenyl)propiolamide.

Melting Point: 92.6°–94.3° C.

¹H-NMR (CDCl₃): δ7.27 (dd, 1H), 7.41 (d, 1H), 7.8 (br, 1H), 8.29 (d, 1H)

Elemental Analysis (%): Calculated for $C_9H_4NOCl_3$: C, 43.50; H, 1.62; N, 5.64 Found: C, 43.43; H, 1.80; N, 5.43

Example 19

N,N-dimethyl-3-chloropropiolamide

By a procedure analogous to Example 1, 0.97 g of N,N-dimethyl-3-chloropropiolamide was obtained as a colorless oil from 3.00 g of N,N-dimethylpropiolamide.

¹H-NMR (CDCl₃): δ2.98 (S, 3H), 3.20 (S, 3H)

Elemental Analysis (%): Calculated for $C_5H_6NOCl$: C, 45.65; H, 4.60; N, 10.65 Found: C, 44.72; H, 4.85; N, 9.92

EXAMPLE 20

N,N-dibutyl-3-chloropropiolamide

By a procedure analogous to Example 1, 2.54 g of N,N-dibutyl-3-chloropropiolamide was obtained as a colorless oil from 3.50 g of N,N-dibutylpropiolamide.

¹H-NMR (CDCl₃): δ0.95 (m, 6H), 1.21–1.42 (m, 4H), 1.43–1.70 (m, 4H), 3.20 (t, 2H), 3.30 (t, 2H)

Elemental Analysis (%): Calculated for $C_{11}H_{18}NOCl$: C, 61.25; H, 8.41; N, 6.49 Found: C, 61.38; H, 8.73; N, 6.01

EXAMPLE 21

1-(3-chloropropioloyl)piperidine

By a procedure analogous to Example 1, 2.20 g of 1-(3-chloropropioloyl)piperidine was obtained as a colorless oil from 3.50 g of 1-propioloylpiperidine ¹H-NMR (CDCl₃): δ1.53–1.72 (m, 6H), 3.56 (t, 2H), 3.67 (t, 2H)

Elemental Analysis (%): Calculated for $C_8H10NOCl$: C, 55.90; H, 5.87; N, 8.16 Found: C, 55.10; H, 5.87; N, 7.93

EXAMPLE 22

N-cyclohexyl-3-chloropropiolamide

By a procedure analogous to Example 1, 2.66 g of N-cyclohexyl-3-chloropropiolamide was obtained as colorless crystals from 2.00 g of N-cyclohexylpropiolamide.

Melting Point: 88.0°–89.0° C.

¹H-NMR (CDCl₃): δ1 .05–1.47 (m, 6H), 1.57–1.77 (m, 2H), 1.89–2.01 (m, 2H), 3.72–3.90 (m, 1H), 5.70 (br, 1H)

Elemental Analysis (%): Calculated for $C_9H_{12}NOCl$: C, 58.23; H, 6.51; N, 7.54 Found: C, 58.40; H, 6.45; N, 7.46

EXAMPLE 23

N-(tert-butyl)-3-bromopropiolamide 0.50 g of N-(tert-butyl)propiolamide was dissolved in 15 ml of methanol, to which 0.17 g of sodium hydroxide was added. 0.64 g of bromine was added dropwise to the mixture while stirring at a room temperature. 50 ml of 5%-aqueous solution of sodium thiosulfate was added to the reaction solution to extract with dichlormethane. The extracted solution was dried and concentrated. The residue was then purified by column chromatography (silica gel, eluent: ethyl acetate/hexane =1/5). Subsequently, 0.55 g of N-(tert-butyl)-3-bromopropiolamide was obtained by means of recrystallization from dichlormethane/hexane.

Melting Point: 113° C.

¹H-NMR (CDCl₃): δ1.36 (s, 9H), 5.65 (br, 1H) IR (KBr) 3280, 2220, 1635

Elemental Analysis (%): Calculated for $C_7H_{10}NOBr$: C, 41.20; H, 4.94; N, 6.86 Found: C, 40.72; H, 4.72; N, 6.68

EXAMPLE 24

N-(n-hexyl)-3-bromopropiolamide 0.61 g of N-(n-hexyl)propiolamide, 1.42 g of N-bromosccinimide, 0.32 of sodium hydroxide, and 0.03 g of tetrabutylammonium bromide were added to 10 ml of acetonitrile. The mixture was stirred overnight at a room temperature.

The reaction solution was poured into water and extracted with ethyl acetate. The ethyl acetate layer was dried and concentrated. The residue was purified by silica gel chromatography (eluent: ethyl acetate/hexane =1/3). Subsequently, 0.82 g of N-(n-hexyl)- 3-bromopropiolamide was obtained by means of recrystallization from hexane/ehhyl acetate.

Melting Point: 64.0°–64.3° C.

¹H-NMR (CDCl₃): δ0.89 (t, 3H), 1.26–1.39 (m, 6H), 1.45–1.55 (m, 2H), 3.29 (dt, 2H), 5.80 (br, 1H)

Elemental Analysis (%): Calculated for $C_3H_{14}NOBr$: C, 46.57; H, 6.08; N, 6.03 Found: C, 46.51; H, 5.99; N, 5.88

Example 25

N-(n-heptyl)-3-bromopropiolamide 0.52 g of N-(n-heptyl)-3-bromopropiolamide was obtained from 0.67 g of N-(n-hephyl)propiolamide.

Melting Point: 68.6° C.

$^1$H-NMR (CDCl$_3$): δ0.88 (t, 3H), 1.28–1.30 (m, 8H), 1.49–1.56 (m, 2H), 3.29 (dt, 2H), 5.80 (br, 1H)

Elemental Analysis (%): Calculated for C$_{10}$H$_{10}$NOBr: C, 48.80; H, 6.55; N, 5.69 Found: C, 48.69; H, 6.60; N, 5.53

EXAMPLE 26

N-(n-octyl)-3-bromopropiolamide

By a procedure analogous to Example 24, 0.71 g of N-(n-octyl)-3-bromopropiolamide was obtained from 0.72 g of N-(n-octyl)propiolamide.

Melting Point: 68.2°–70.0° C.

$^1$H-NMR (CDCl$_3$): δ0.88 (t, 3H), 1.28–1.30 (m, 10H), 1.49–1.55 (m, 2H), 3.29 (dt, 2H), 5.80 (br, 1H)

Elemental Analysis (%): Calculated for C$_{11}$H$_{18}$NOBr: C, 50.78; H, 6.97; N, 5.38 Found: C, 50.66; H, 7.06; N, 5.22

EXAMPLE 27

N-(n-nonyl)-3-bromopropiolamide

By a procedure analogous to Example 24, 0.82 g of N-(n-nonyl)-3-bromopropiolamide was obtained from 0.78 g of N-(n-nonyl)propiolamide.

Melting Point: 75.7°–7 6.1° C.

$^1$H-NMR (CDCl$_3$): δ0.8 5 (t, 3H), 1.26 (m, 12H), 1.47–1.51 (m, 2H), 3.28 (dt, 2H), 5.80 (br, 1H)

Elemental Analysis (%): Calculated for C$_{12}$H$_{20}$NOBr: C, 52.56; H, 7.35; N, 5.11 Found: C, 52.36; H, 7.45; N, 4.90

EXAMPLE 28

N-(n-decyl)-3-bromopropiolamide

By a procedure analogous to Example 24, 0.85 g of N-(n-decyl)-3-bromopropiolamide was obtained from 0.84 g of N-(n-decyl)propiolamide.

Melting Point: 75.8°–76.4° C.

$^1$H-NMR (CDCl$_3$): δ0.88 (t, 3H), 1.26 (m, 14H), 1.52 (m, 2H), 3.29 (dt, 2H), 5.80 (br, 1H)

Elemental Analysis (%): Calculated for C$_{13}$H22NOBr: C, 54.17; H, 7.69; N, 4.86 Found: C, 54.11; H, 7.90; N, 4.72

EXAMPLE 29

3-bromopropiolamide 6.50 g of propiolamide and 20.10g of N-bromosuccinimide were dissolved in 200 ml of acetone, to which 1.59 g silver nitrate was added at a room temperature. The mixture was stirred for 1.5 hours. 5 ml of water was added to the reaction solution, which was concentrated under reduced pressure. The residue was added ethyl acetate and water. The organic phase was dried over anhydrous magnesium sulfate and was then concentrated under reduced pressure to remove the solvent. The residue was purified by silica gel chromatography (eluent: ethyl acetate/hexane=1/3). Subsequently, 4.82 g of 3-bromopropiolamide was obtained by means of recrystallization from the ethyl acetate/hexane solution.

Melting Point: 136.0°–137.0° C.

$^1$H-NMR (CDCl$_3$): δ5.8 (s, 2H),

Elemental Analysis (%): Calculated for C$_3$H$_2$NOBr: C, 24.35; H, 1.36; N, 9.47 Found: C, 24.40; H, 1.29; N, 9.46

EXAMPLE 30

N-methyl-3-bromopropiolamide

By a procedure analogous to Example 29, 7.65 g of N-methyl-3-bromopropiolamide was obtained as colorless crystals from 6.56 g of N-methylpropiolamide.

Melting Point: 150.5°–1.51.5° C.

$^1$H-NMR (CDCl$_3$): δ3.88 (d, 3H), 6.09 (br, 1H)

Elemental Analysis (%): Calculated for C$_4$H$_4$NOBr: C, 29.66; H, 2.49; N, 8.65 Found: C, 29.77; H, 2.45; N, 8.79

EXAMPLE 31

N-ethyl-3-bromopropiolamide

By a procedure analogous to Example 29, 4.08 g of N-ethyl-3-bromopropiolamide was obtained as colorless crystals from 3.50 g of N-ethylpropiolamide.

Melting Point: 64.5°–66.0° C.

$^1$H-NMR (CDCl$_3$): δ1.18 (t, 3H), 3.27–3.41 (dt, 2H), 6.02 (br, 1H)

Elemental Analysis (%): Calculated for C$_5$H$_6$NOBr: C, 34.12; H, 3.44; N, 7.96 Found: C, 33.90; H, 3.23; N, 8.04

EXAMPLE 32

N-propyl-3-bromopropiolamide

By a procedure analogous to Example 29, 4.00 g of N-propyl-3-bromopropiolamide was obtained as colorless crystals from 3.50 g of N-propylpropiolamide.

Melting Point: 61.5°–63.0° C.

$^1$H-NMR (CDCl$_3$): δ0.93 (t, 3H), 1.48–1.67 (m, 2H), 3.28 (dt, 2H), 5.97 (br, 1H)

Elemental Analysis (%): Calculated for C$_6$H$_8$NOBr: C, 37.92; H, 4.24; N, 7.37 Found: C, 37.92; H, 4.23; N, 7.62

EXAMPLE 33

N-butyl-3-bromopropiolamide

By a procedure analogous to Example 29, 3.34 g of N-butyl-3-bromopropiolamide was obtained as colorless crystals from 3.00 g of N-butylpropiolamide.

Melting Point: 73.6°–75.2° C.

$^1$H-NMR (CDCl$_3$): δ0.93 (t, 3H), 1.27–1.60 (m, 4H), 3.00 (dt, 2H), 6.15 (br, 1H)

Elemental Analysis (%): Calculated for C$_7$H$_{10}$NOBr: C, 41.20; H, 4.94; N, 6.86; Br, 39.16 Found: C, 41.04; H, 4.82; N, 7.09; Br, 39.23

EXAMPLE 34

N-pentyl-3-bromopropiolamide

By a procedure analogous to Example 29, 3.17 g of N-pentyl-3-bromopropio. lamide was obtained as colorless crystals from 3.00 g of N-pentylpropiolamide.

Melting Point: 59.0°–60.2° C.

¹H-NMR (CDCl₃): δ0.93 (t, 3H), 1.20–1.60 (m, 6H), 3.30 (dt, 2H), 5.80 (br, 1H)

Elemental Analysis (%): Calculated for C₈H₁₂NOBr: 44.06; H, 5.55; N, 6.42; Br, 36.64 Found: C, 44.06; H, 5.61; N, 6.63; Br, 36.53

EXAMPLE 35

N-dodecyl-3-bromopropiolamide

By a procedure analogous to Example 29, 2.70 g of N-dodecyl-3-bromopropiolamide was obtained as colorless crystals from 4.74 g of N-dodecylpropiolamide.

Melting Point: 82.5°–83.5° C.

¹H-NMR (CDCl₃): δ0.88 (t, 3H), 1.30 (br, 18H), 1.51 (m, 2H), 3.40 (dt, 2H), 5.84 (br, 1H)

Elemental Analysis (%): Calculated for C₁₅H₂₆NOBr: C, 56.96; H, 8.29; N, 4.43 Found: C, 56.79; H, 8.35; N, 4.38

EXAMPLE 36

N-tetradecyl-3-bromopropiolamide

By a procedure analogous to Example 29, 1.64 g of N-hetradecyl-3-bromopropiolamide was obtained as colorless crystals from 2.83 g of N-tetradecylpropiolamide.

Melting Point: 86.5°–87.5° C.

¹H-NMR (CDCl₃): δ0.90 (t, 3H), 1.29 (br, 22H), 1.50 (m, 2H), 3.29 (dt, 2H), 5.90 (br, 1H)

Elemental Analysis (%): Calculated for C₁₇H₃₀NOBr: C, 59.30; H, 8.78; N, 4.07 Found: C, 59.39; H, 8.67; N, 4.06

EXAMPLE 37

N-octadecyl-3-bromopropiolamide

By a procedure analogous to Example 29, 1.88 g of N-octadecyl-3-bromopropiolamide was obtained as colorless cryshals from 6.00 g of N-octadecylpropiolamide.

Melting Point: 91.0°–92.0° C.

¹H-NMR (CDCl₃): δ0.89 (t, 3H), 1.29 (br, 30H), 1.52 (m, 2H), 3.50 (dt, 2H), 5.8 (br, 1H)

Elemental Analysis (%): Calculated for C₂₁H₃₈NOBr: C, 62.99; H, 9.56; N, 3.50 Found: C, 62.96; H, 9.47; N, 3.53

EXAMPLE 38

N-(m-chlorophenyl)-3-bromopropiolamide

By a procedure analogous to Example 29, 0.67 g of N-(m-chlorophenyl)-3-bromopropiolamide was obtained as colorless crystals from 0.54 g of N-(m-chlorophenyl) propiolamide.

Melting Point: 116.9°–117.8° C.

¹H-NMR (CDCl₃): δ7.10–7.39 (m, 3H), 7.63 (t, 1H), 7.7 (br, 1H)

Elemental Analysis (%): Calculated for C₉H₅NOBr: C, 41.82; H, 1.95; N, 5.42 Found: C, 41.58; H, 2.00; N, 5.37

EXAMPLE 39

N-(p-chlorophenyl)-3-bromopropiolamide

By a procedure analogous to Example 29, 0.60 g of N-(p-chlorophenyl)-3-bromopropiolamide was obtained as colorless crystals from 0.54 g of N-(p-chlorophenyl)propiolamide.

Melting Point: 89.3°–90.6° C.

¹H-NMR (CDCl₃): δ7.30 (dt, 2H), 7.46 (d, 2H)

Elemental Analysis (%): Calculated for C₉H₅NOBrCl: C, 41.82; H, 1.95; N, 5.42 Found: C, 41.57; H, 1.94; N, 5.41

EXAMPLE 40

N-(m-trifluoromethylphenyl)-3-bromopropiolamide

By a procedure analogous to Example 29, 0.85 g of N-(m-trifluoromethylphenyl)-3-bromopropiolamide was obtained as brown amorphous solid from 0.64 g of N-(m-trifluoromethylphenyl)propiolamide.

¹H-NMR (CDCl₃): δ7.39–7.51 (m, 2H), 7.67–7.78 (m, 3H)

Elemental Analysis (%): Calculated for C₁₀H₅NOBrF₃: C, 41.13; H, 1.73; 4.80 Found: C, 40.71; H, 1.76; N, 4.63

EXAMPLE 41

N-(m-nitrophenyl)-3-bromopropiolamide

By a procedure analogous to Example 29, 0.74 g of N-(m-nitrophenyl)-3-bromopropiolamide was obtained as yellow crystals from 0.57 g of N-(m-nitrophenyl)propiolamide.

Melting Point: 175.0°–177.0° C.

¹H-NMR (Acetone-d6): δ7.62–7.78 (m, 1H), 7.99–8.15 (m, 2H), 8.69–8.78 (m, 1H), 10.3 (br, 1H)

Elemental Analysis Calculated for C₉H₅N₂O₃Br: C, 40.18; H, 1.87; N, 10.41 Found: C, 40.01; H, 1.98; N, 10.13

EXAMPLE 42

N-(2,4-dichlorophenyl)-3-bromopropiolamide

By a procedure analogous to Example 29, 0.43 g of N-(2,4-dichlorophenyl)-3-bromopropiolamide was obtained as colorless crystals from 0.35 g of N-(m-chlorophenyl)propiolamide.

Melting Point: 89.3°–90.6° C.

¹H-NMR (CDCl₃): δ7.26 (dd, 1H), 7.41 (d, 1H), 7.8 (br, 1H), 8.28 (d, 1H)

Elemental Analysis (%): Calculated for C₉H₄NOBrC₁₂: C, 36.90; H, 1.38; N, 4.78 Found: C, 36.81; H, 1.40; N, 4.40

EXAMPLE 43

N-(2-pyridylethyl) -3-bromopropiolamide

By a procedure analogous to Example 29, 0.42 g of N-(2-pyridylethyl)-3-bromopropiolamide was obtained as a colorless oil from 1.03 g of N-(2-pyridylethyl) propiolamide.

¹H-NMR (CDCl₃): δ3.00 (t, 2H), 3.72 (dr, 2H), 7.15 (br, 1H), 7.15–7.18 (m, 2H), 7.64 (ddd, 1H), 8.53–8.57 (m, 1H)

Elemental Analysis (%): Calculated for C₁₀H₉N₂OBr:C, 47.46; H, 3.58; N, 11.07 Found: C, 47.41; H, 3.56; N, 11.07

EXAMPLE 44

N,N-dimethyl-3-bromopropiolamide

By a procedure analogous to Example 29, 2.28 g of N,N-dimethy 1-3-bromopropiolamide was obtained as colorless crystals from 3.00 g of N,N-dimethylpropiolamide.

Melting Point: 94.0°–95.5° C.

¹H-NMR (CDCl₃): δ2.98 (S, 3H), 3.21 (S, 3H)

Elemental Analysis (%): Calculated for C₅H₆NOBr: C, 34.12; H, 3.44; N, 7.96 Found: C, 33.96; H, 3.53; N, 7.90

EXAMPLE 45

N,N-dibutyl-3-bromopropiolamide

By a procedure analogous to Example 29, 4.53 g of N,N-dibutyl-3-bromopropiolamide was obtained as a colorless oil from 3.50 g of N,N-dibutylpropiolamide.

¹H-NMR (CDC13): 60.94 (m, 6H), 1.21–1.42 (m, 4H), 1.43–1.70 (m, 4H), 3.40 (t, 2H), 3.50 (t, 2H)

Elemental Analysis (%): Calculated for C₁₁H₁₈NOBr: C, 50.78; H, 6.97; N, 5.38 Found: C, 49.90; H, 7.06; N, 5.29

EXAMPLE 46

1-(3-bromopropioloyl)piperidine

By a procedure analogous to Example 29, 2.35 g of 1-(3-bromopropioloyl)piperidine was obtained colorless crystals from 3.00 g of 1-propioloylpiperidine.

Melting Point: 66.5°–67.5° C.

¹H-NMR (CDCl₃): δ1.50–1.73 (m, 6H), 3.56 (t, 2H), 3.68 (t, 2H)

Elemental Analysis (%): Calculated for C₈H₁₀NOBr: C, 44.47; H, 4.66; N, 6.48 Found: C, 44.18; H, 4.66; N, 6.49

EXAMPLE 47

N-cyclohexyl-3-bromopropiolamide

By a procedure analogous to Example 29, 2.55 g of N-cyclohexyl-3-bromopropiolamide was obtained as colorless crystals from 2.00 g of N-cyclohexylpropiolamide.

Melting Point: 108.0°–109.0° C.

¹H-NMR (CDCl₃): δ1.04–1.47 (m, 6H), 1.57–1.77 (m, 2H), 1.89–2.01 (m, 2H), 3.72–3.90 (m, 1H), 5.76 (br, 1H)

Elemental Analysis (%): Calculated for C₉H₁₂NOBr: C, 46.98; H, 5.26; N, 6.09 Found: C, 47.03; H, 5.16; N, 6.02

Test Example 1

Measurement on Antibacterial/Antifungal Activity (Measurement on Inhibition Zone)

A common paper disc method was used to perform activity tests. More specifically, a paper disc of 8 mm in diameter was immersed with water or a methanol solution of the present compound (concentration: 1000 μg/ml) and was dried for use.

Test strains were: *Staphylococcus aureus* (IFO-12732, hereinafter abbreviated as Sta.) and *Bacillus subtilis* (IFO-13719, hereinafter abbreviated as Bac.) as bacteria, *Saccharomyces cerevisiae* (IFO-021 0; Sac. ) and *Candida albicans* (IFO-0583; Can.) as the yeast, and *Aspergillus niger* (IFO-4407; Asp. ), *Penicillium citrinum* (IFO-7784; Pen.), *Tyromyces palustris* (IFO-30339; Tyr.), and *Coriolus versicolor* (IF-30340; Cor.) as fungi. Tyr. and Cor. are wood rot fungi.

A test medium used as following agar media. More specifically, Trypticase Soy Agar (TSA) medium was used for Sta., Bac., and Esc. Yeast Nitrogen Base (YNB) agar medium was used for Sac. and Can. Sabouraud Dextrose Agar (SDA) medium was used for Asp. and Pen. Potato Dextrose Agar (PDA) medium was used for Try. and Cor.

The antibacterial/antifungal activities were measured by means of determining a diameter of an inhibition zone generated around the paper disc. The results are given in Table 1 through Table 6 below. Indications on the activities are as follows:

−: No inhibition zone found
+: 9–20 mm inhibition zone
++: 21–40 mm inhibition zone
+++: 41 mm or larger inhibition zone

TABLE 1

| Test strain | Example Compound |  |  |  |  |  |
|---|---|---|---|---|---|---|
| | 1 | 2 | 3 | 4 | 5 | 6 |
| Sta. | ++ | ++ | ++ | ++ | + | ++ |
| Bac. | + | + | + | + | + | ++ |
| Sac. | ++ | ++ | ++ | + | + | ++ |
| Can. | ++ | ++ | ++ | + | − | ++ |
| Asp. | ++ | ++ | + | + | + | ++ |
| Pen. | +++ | +++ | ++ | ++ | + | ++ |
| Tyr. | +++ | +++ | +++ | +++ | ++ | +++ |
| Cor. | +++ | +++ | ++ | ++ | + | ++ |

TABLE 2

| Test strain | Example Compound |  |  |  |
|---|---|---|---|---|
| | 7 | 8 | 9 | 10 |
| Sta. | ++ | + | + | + |
| Bac. | + | ++ | ++ | + |
| Sac. | ++ | ++ | ++ | ++ |
| Can. | ++ | ++ | ++ | ++ |
| Asp. | ++ | ++ | ++ | ++ |
| Pen. | +++ | ++ | ++ | +++ |
| Tyr. | +++ | ++ | +++ | +++ |
| Cor. | +++ | +++ | +++ | ++ |

TABLE 3

| Test strain | Example Compound |  |  |  |  |  |  |  |  |
|---|---|---|---|---|---|---|---|---|---|
| | 14 | 15 | 16 | 17 | 18 | 19 | 20 | 21 | 22 |
| Sta. | + | + | + | + | + | ++ | + | + | + |
| Bac. | + | + | + | + | + | + | ++ | + | + |
| Sac. | ++ | ++ | ++ | ++ | ++ | ++ | ++ | + | + |
| Can. | ++ | ++ | ++ | + | ++ | ++ | + | + | ++ |
| Asp. | + | + | ++ | + | ++ | +++ | +++ | ++ | ++ |
| Pen. | ++ | ++ | ++ | ++ | ++ | +++ | +++ | ++ | ++ |
| Tyr. | ++ | ++ | ++ | ++ | ++ | +++ | +++ | ++ | +++ |
| Cor. | ++ | ++ | ++ | + | ++ | +++ | +++ | +++ | ++ |

TABLE 4

| Test strain | Example Compound | | | |
|---|---|---|---|---|
| | 23 | 24 | 25 | 26 |
| Sta. (IFO-12732) | + | ++ | ++ | + |
| Bac. (IFO-13719) | + | + | + | + |
| Sac. (IFO-0210) | − | ++ | ++ | + |
| Can. (IFO-0583) | + | ++ | ++ | + |
| Asp. (IFO-4407) | + | ++ | + | + |
| Pen. (IFO-7784) | ++ | ++ | ++ | ++ |
| Tyr. (IFO-30339) | ++ | +++ | +++ | ++ |
| Cor. (IFO-30340) | ++ | +++ | ++ | ++ |

TABLE 5

| Test strain | Example Compound | | | | | |
|---|---|---|---|---|---|---|
| | 29 | 30 | 31 | 32 | 33 | 34 |
| Sta. (IFO-12732) | ++ | ++ | + | ++ | ++ | ++ |
| Bac. (IFO-13719) | + | + | + | ++ | + | + |
| Sac. (IFO-0210) | ++ | ++ | + | + | + | ++ |
| Can. (IFO-0583) | ++ | ++ | ++ | ++ | ++ | ++ |
| Asp. (IFO-4407) | ++ | ++ | ++ | ++ | ++ | ++ |
| Pen. (IFO-7784) | ++ | +++ | ++ | ++ | ++ | ++ |
| Tyr. (IFO-30339) | +++ | +++ | +++ | +++ | +++ | +++ |
| Cor. (IFO-30340) | ++ | ++ | ++ | ++ | ++ | ++ |

TABLE 6

| Test strain | Example Compound | | | | | | | | | |
|---|---|---|---|---|---|---|---|---|---|---|
| | 38 | 39 | 40 | 41 | 42 | 43 | 44 | 45 | 46 | 47 |
| Sta. (IFO-12732) | ++ | + | ++ | + | + | + | ++ | ++ | + | ++ |
| Bac. (IFO-13719) | + | + | + | + | + | + | + | ++ | + | + |
| Sac. (IFO-0210) | ++ | ++ | ++ | + | ++ | − | + | + | + | + |
| Can. (IFO-0583) | ++ | ++ | ++ | + | ++ | − | ++ | + | ++ | ++ |
| Asp. (IFO-4407) | + | + | + | + | + | + | ++ | +++ | ++ | ++ |
| Pen. (IFO-7784) | ++ | ++ | ++ | + | ++ | + | ++ | +++ | ++ | ++ |
| Tyr. (IFO-30339) | +++ | +++ | ++ | ++ | ++ | ++ | +++ | +++ | ++ | +++ |
| Cor. (IFO-30340) | ++ | + | ++ | + | + | ++ | +++ | +++ | +++ | ++ |

As apparent from Tables 1 through 6, the present compounds exhibit strong antibacterial or antifungal activities: the compound of Example 1 particularly to Sta., Sac., Can., Asp., Pen., Tyr., and Cor., the compound of Example 2 particularly to Sta., Sac., Can., Asp., Pen., Tyr., and Cor., the compound of Example 3 particularly to Sta., Sac., Can., Pen., Tyr., and Cor., the compound of Example 4 particularly to Sta., and Pen., the compound of Example 5 particularly to Tyr., the compound of Example 6 particularly to Sta., Bac., Sac., Can., Asp., Pen., Tyr., and Cot., the compound of Example 7 particularly to Sta., Sac., Can., Asp., Pen., Tyr., and Cor., the compound of Example 8 particularly to Bac., Sac., Can., Asp., Pen., Tyr., and Cor., the compound of Example 9 particularly to Bac., Sac., Can., Asp., Pen., Tyr., and Cor., the compound of Example 10 particularly to Sac., Can., Asp., Pen., Tyr., and Cor., the compound of Example 14 particularly to Sac., Can., Pen., Tyr., and Cor., the compound of Example 15 particularly to Sac., Can., Pen., Tyr., and Cor., the compound of Example 16 particularly to Sac., Can., Asp., Pen., Tyr., and Cor., the compound of Example 17 particularly to Sac., Pen., and Tyr., the compound of Example 18 particularly to Sac., Can., Asp., Pen., Tyr., and Cor., the compound of Example 19 particularly to Sta., Sac., Can., Asp., Pen., Tyr., and Cor., the compound of Example 20 particularly to Bac., Sac., Asp., Pen., Tyr., Cor., the compound of Example 21 particularly to Asp., Pen., Tyr., and Cor., the compound of Example 22 particularly to Can., Asp., Pen., Tyr., and Cor., the compound of Example 23 particularly to Pen., Tyr., and Cor., the compound of Example 24 particularly to Sta., Sac., Can., Asp., Pen., Tyr., and Cor., the compound of Example 25 particularly to Sta., Sac., Can., Pen., Tyr., and Cor., the compound of Example 26 particularly to Pen., Tyr., and Cot., the compound of Example 29 particularly to Sta., Sac., Can., Asp., Pen., Tyr., and Cor., the compound of Example 30 particularly to Sta., Sac., Can., Asp., Pen., Tyr., and Cor., the compound of Example 31 particularly to Can., Asp., Pen., Tyr., and Cot., the compound of Example 32 particularly to Sta., Bac., Can., Asp., Pen., Tyr., and Cor., the compound of Example 33 particularly to Sta., Can., Asp., Pen., Tyr., and Cor., the compound of Example 34 particularly to Sta., Sac., Can., Asp., Pen., Tyr., and Cor., the compound of Example 38 particularly to Sta., Sac., Can., Pen., Tyr., and Cor., the compound of Example 39 particularly to Sac., Can., Pen., and Tyr., the compound of Example 40 particularly to Sta., Sac., Can., Pen., Tyr., and Cor., the compound of Example 41 particularly to Tyr., the compound of Example 42 particularly to Sac., Can., Pen., and Tyr., the compound of Example 43 particularly to Tyr., and Cor., the compound of Example 44 particularly to Sta., Can., Asp., Pen., Tyr., and Cor., the compound of Example 45 particularly to Sta., Bac., Asp., Pen., Tyr., and Cor., the compound of Example 46 particularly to Can., Asp., Pen., Tyr., and Cor., and the compound of Example 47 particularly to Sta., Can., Asp., Pen., Tyr., and Cor.

Test Example 2

Measurement on Antibacterial/antifungal Activities (MIC Measurement)

The minimum inhibition concentration (MIC) was measured by using an agar medium dilution method. The media used were: POTATO DEXTROSE AGAR (available from Difco, Co.) containing 0.5%-yeast extract (available from Difco, Co.) when the tested fungi were bacteria, yeast, *Cladosporium cladosporioides*, *Tyromyces palustris*, and *Coriolus versicolor*, and SABOURAUD DEXTROSE AGAR (Difco) when the tested fungi were other fungi. Cultivation was made for 24 hours at 28° C. when the tested fungi were bacteria and yeast; for 72 hours at 24° C. when the tested fungi were fungus such as *Cladosporium cla-*

*dosporioides, Tyromyces palustris,* and *Coriolus versicolor,* and for 48 hours at 28° C. for other fungus.

The test strains used were: *Staphylococcus aureus* (IFO-1 2732; Sta.), and *Bacillus subtilis* (IFO-3719; Bac.) as the gram-positive bacteria, *Pseudomonas aeruginosa* (IFO-12689; Pse.), and *Escherichia coli* (IFO-3301; Esc.) as the gram-negative bacteria, *Saccharomyces cerevisiae* (IFO-0210; Sac.), and *Candida albicans* (IFO-0583; Can.,) as the yeast, *Aspergillus niger* (IFO-4407; Asp.), *Penicillium citrinum* (IFO-7784; Pen.), *Cladosporium cladosporioides* (IFO-6369; Cla.), *Aureobasidium pullulans* (IFO-6353; Aur.), *Chaetomium globossum* (IFO-6347; Cha.), *Trichoderma viride* (IFO-31137; Tri.), and *Paecilomyces variotti* (IFO-30539; Pae) as the fungi, and *Tyromyces palustris* (IFO-30339; Tyr.) and *Coriolus versicolor* (IFO-30340; Cot.) as the wood rot fungi. The results are given in Table 7 through Table 11. The values in the tables represent MIC (μg/ml).

TABLE 7

| Test | Example Compound | | |
|---|---|---|---|
| strain | 7 | 29 | 30 |
| Pse. | 12.5 | 3.13 | 25 |
| Esc. | 25 | 3.13 | 50 |

TABLE 8

| Test | Example Compound | | | | | | | | | |
|---|---|---|---|---|---|---|---|---|---|---|
| strain | 1 | 2 | 3 | 4 | 5 | 6 | 7 | 8 | 9 | 10 |
| Sta. | 1.56 | 1.56 | 0.78 | 0.78 | 0.78 | 6.25 | 6.25 | 12.5 | 12.5 | 6.25 |
| Bac. | 3.13 | 3.13 | 1.56 | 1.56 | 1.56 | 6.25 | 12.5 | 12.5 | 12.5 | 12.5 |
| Sac. | 6.25 | 6.25 | 3.13 | 3.13 | 3.13 | 6.25 | 12.5 | 12.5 | 12.5 | 12.5 |
| Can. | 6.25 | 6.25 | 6.25 | 3.13 | 12.5 | 6.25 | 12.5 | 50 | 50 | 12.5 |
| Asp. | 0.78 | 1.56 | 1.56 | 3.13 | 6.25 | 1.56 | 6.25 | 6.25 | 12.5 | 6.25 |
| Pen. | 3.13 | 1.56 | 1.56 | 1.56 | 3.13 | 6.25 | 3.13 | 6.25 | 12.5 | 6.25 |
| Cla. | 0.39 | 0.78 | 0.39 | 0.78 | 0.39 | 0.39 | 0.78 | 3.13 | 3.13 | 0.78 |
| Aur. | 3.13 | 3.13 | 3.13 | 3.13 | 25 | 3.13 | 1.56 | 3.13 | 12.5 | 6.25 |
| Cha. | 1.56 | 0.78 | 0.39 | 1.56 | 1.56 | 1.56 | 6.25 | 6.25 | 6.25 | 6.25 |
| Tri. | 6.25 | 3.13 | 3.13 | 3.13 | 3.13 | 3.13 | 12.5 | 25 | 25 | 12.5 |
| Pae. | 6.25 | 3.13 | 3.13 | 6.25 | 6.25 | 6.25 | 6.25 | 12.5 | 25 | 12.5 |
| Tyr. | 0.78 | 0.39 | 0.39 | 0.39 | 0.39 | 1.56 | 1.56 | 3.13 | 3.13 | 1.56 |
| Cor. | 0.39 | <0.18 | 0.39 | 0.78 | 1.56 | 0.78 | 3.13 | 3.13 | 3.13 | 1.56 |

TABLE 9

| Test | Example Compound | | | | | | | | |
|---|---|---|---|---|---|---|---|---|---|
| strain | 24 | 25 | 26 | 29 | 30 | 31 | 32 | 33 | 34 |
| Sta. | 3.13 | 1.56 | 6.25 | 3.13 | 12.5 | 12.5 | 25 | 12.5 | 6.25 |
| Bac. | 6.25 | 6.25 | 12.5 | 12.5 | 25 | 12.5 | 12.5 | 12.5 | 6.25 |
| Sac. | 6.25 | 6.25 | 12.5 | 12.5 | 12.5 | 25 | 25 | 12.5 | 6.25 |
| Can. | 3.13 | 12.5 | 12.5 | 12.5 | 50 | 100 | 50 | 25 | 6.25 |
| Asp. | 1.56 | 1.56 | 3.13 | 12.5 | 12.5 | 12.5 | 12.5 | 6.25 | 3.13 |
| Pen. | 6.25 | 3.13 | 6.25 | 6.25 | 6.25 | 6.25 | 12.5 | 6.25 | 6.25 |
| Cla. | 1.56 | 0.78 | 1.56 | 1.56 | 1.56 | 1.56 | 1.56 | 1.56 | 0.78 |
| Aur. | 3.13 | 6.25 | 12.5 | 3.13 | 3.13 | 3.13 | 6.25 | 12.5 | 6.25 |
| Cha. | 1.56 | 0.78 | 1.56 | 6.25 | 6.25 | 6.25 | 12.5 | 6.25 | 1.56 |
| Tri. | 12.5 | 25 | 12.5 | 12.5 | 12.5 | 12.5 | 25 | 12.5 | 6.25 |
| Pae. | 6.25 | 6.25 | 6.25 | 12.5 | 12.5 | 12.5 | 12.5 | 12.5 | 6.25 |
| Tyr. | 1.56 | 0.78 | 1.56 | 1.56 | 3.13 | 3.13 | 3.13 | 3.13 | 1.56 |
| Cor. | 0.39 | <0.18 | 1.56 | 1.56 | 6.25 | 3.13 | 3.13 | 3.13 | 1.56 |

TABLE 10

| Test strain | Example Compound | | | | | | | | | |
|---|---|---|---|---|---|---|---|---|---|---|
| | 14 | 15 | 16 | 17 | 18 | 38 | 39 | 40 | 41 | 42 |
| Sta. | 1.56 | 3.13 | 1.56 | 3.13 | 1.56 | 1.56 | 1.56 | 1.56 | 3.13 | 1.56 |
| Bac. | 1.56 | 3.13 | 3.13 | 6.25 | 1.56 | 3.13 | 3.13 | 3.13 | 6.25 | 1.56 |
| Sac. | 3.13 | 3.13 | 6.25 | 6.25 | 3.13 | 3.13 | 3.13 | 6.25 | 25 | 6.25 |
| Can. | 6.25 | 6.25 | 6.25 | 25 | 6.25 | 6.25 | 3.13 | 12.5 | 50 | 12.5 |
| Asp. | 12.5 | 6.25 | 25 | 25 | 12.5 | 12.5 | 12.5 | 25 | 50 | 12.5 |
| Pen. | 3.13 | 3.13 | 12.5 | 6.25 | 3.13 | 3.13 | 6.25 | 6.25 | 12.5 | 3.13 |
| Cla. | 0.78 | 1.58 | 3.13 | 3.13 | 1.56 | 1.56 | 1.56 | 3.13 | 6.25 | 6.25 |
| Aur. | 12.5 | 12.5 | 25 | 12.5 | 12.5 | 12.5 | 12.5 | 25 | 25 | 25 |
| Cha. | 3.13 | 3.13 | 6.25 | 12.5 | 6.25 | 0.78 | 1.56 | 1.56 | 3.13 | 3.13 |
| Tri. | 12.5 | 12.5 | 25 | 25 | 12.5 | 6.25 | 6.25 | 12.5 | 25 | 12.5 |
| Pae. | 6.25 | 3.13 | 12.5 | 12.5 | 6.25 | 6.25 | 3.13 | 12.5 | 25 | 6.25 |
| Tyr. | 0.39 | 1.56 | 1.56 | 0.78 | 0.39 | 1.56 | 0.78 | 3.13 | 3.13 | 0.39 |
| Cor. | 0.78 | 1.56 | 1.56 | 3.13 | 0.78 | 1.56 | 1.56 | 6.25 | 6.25 | 1.56 |

TABLE 11

| Test strain | Example Compound | | | |
|---|---|---|---|---|
| | 19 | 21 | 44 | 46 |
| Sta. | 0.78 | 3.13 | 6.25 | 6.25 |
| Bac. | 25 | 6.25 | 25 | 12.5 |
| Asp. | 1.56 | 6.25 | 3.13 | 6.25 |
| Pen. | 12.5 | 12.5 | 12.5 | 25 |
| Cla. | 1.56 | 1.56 | 1.56 | 3.13 |
| Aur. | 1.56 | 3.13 | 3.13 | 6.25 |
| Cha. | 3.13 | 6.25 | 3.13 | 6.25 |
| Pae. | 12.5 | 25 | 12.5 | 25 |
| Tyr. | 3.13 | 1.56 | 3.13 | 3.13 |
| Cor. | 3.13 | 1.56 | 3.13 | 3.13 |

(1) The compound (Ia) in which $R_3$ is a linear $C_{1-10}$ alkyl group, and $R_4$ is a hydrogen atom (i.e., the compounds in Examples 1 through 10), in particular, a compound in which $R_3$ is a linear $C_{6-10}$ alkyl group and $R_4$ is a hydrogen atom (i.e., the compounds in Examples 1 through 5) exhibits superior antibacterial activities to a gram-positive bacterium (e.g., Sta., and Bac.) [Table 8].

(2) The compound (Ia) in which $R_3$ is a methyl group and $R_4$ is a hydrogen atom (i.e., the compound in Example 7) exhibits superior antibacterial activities to a gram-negative bacterium (e.g., Psc., Esc.) [Table 7].

(3) The compound (Ia) in which $R_3$ is a linear $C_{1-10}$ alkyl group and $R_4$ is a hydrogen atom (i.e., the compounds in Examples 1 through 10) exhibits superior antifungal activities to fungi (e.g., the yeast (e.g., Sac., and Can.), Asp., Pen., Cla., Aur., Cha., Tri., and Pae., and the wood rot fungi (e.g., Tyr., and Cot.) [Table 8] . In particular, it is the compound (Ia) in which $R_3$ is a methyl group, a n-butyl group, a n-pentyl group, a n-hexyl group, a n-heptyl group, a n-octyl group, a n-nonyl group, or a n-decyl group, and $R_4$ is a hydrogen atom (i.e., the compounds in Examples 1 through 7 and 10) that exhibits superior antifungal activities to the yeast (e.g., Sac., and Can.) [Table 8].

(4) The compound (Ia) in which $R_3$ is a phenyl group substituted by chlorine, a trifluoromethyl group or a nitro group and $R_4$ is a hydrogen atom (i.e., the compounds in Examples 14 through 18) exhibits superior antibacterial and antifungal activities to the gram-positive bacteria (e.g., Sta., and Bac.) and the fungus [the yeast (e.g., Sac., and Can.), Asp., Pen., Cla., Aur., Cha., Tri., and Pae., and the wood rot fungi (e.g., Tyr., and Cor.)] [Table 10].

(5) The compound (Ia) in which $R_3$ and $R_4$ are each a methyl group, or $R_3$ and $R_4$ form a 1-piperidyl group in cooperation with a nitrogen atom adjacent thereto (i.e., the compounds in Examples 19 and 21) exhibits superior antibacterial and antifungal activities to the gram-positive bacteria (e.g., Sta., and Bac.) the fungus [preferably, those other than the yeast (e.g., Asp., Pen., Cla., Aur., Cha., and Pae.), and the wood rot fungi (e.g., Tyr., and Cor.)] [Table 11].

(6) The compound (Ib) in which $R_5$ is a hydrogen atom or a linear $C_{1-10}$ alkyl group and $R_6$ is a hydrogen atom (i.e., the compounds in Examples 24 through 34), in particular, the compound (Ib) in which $R_5$ is a hydrogen atom or a linear $C_{6-10}$ alkyl group and $R_6$ is a hydrogen atom (i.e., the compounds in Examples 24 through 26, 29 through 34) exhibits superior antibacterial activities to the gram-positive bacteria (e.g., Sta., and Bac.) [Table 9].

(7) The compound (Ib) in which $R_5$ is a hydrogen atom or a methyl group and $R_6$ is a hydrogen atom (i.e., the compounds in Examples 29 and 30), in particular, the compounds (Ib) in which $R_5$ and $R_6$ are each a hydrogen atom (i.e., the compound in Example 29) exhibits superior antibacterial activities to the gram-negative bacteria (e.g., Pse., and Esc.) [Table 7].

(8) The compound (Ib) in which $R_5$ is a hydrogen atom or a linear $C_{1-10}$ alkyl group and $R_6$ is a hydrogen atom (i.e., the compounds in Examples 24 through 34) exhibits superior antifungal activities to fungi (e.g., yeast (e.g., Sac., and Can.), Asp., Pen., Cla., Aur., Cha., Tri., and Pae., and the wood rot fungi (e.g., Tyr., and Cor.) [Table 9]. In particular, it is the compound (Ib) in which $R_5$ is a hydrogen atom, a n-pentyl group, a n-hexyl group, a n-heptyl group, or a n-octyl group, and $R_6$ is a hydrogen atom (i.e., the compounds in Examples 24 through 26, 29, and 34) that exhibits superior antifungal activities to the yeast (e.g., Sac., and Can.). For example, it is the compound (Ib) in which $R_5$ is a hydrogen atom or a linear $C_{1-8}$ alkyl group and $R_6$ is a hydrogen atom (i.e., the compounds in Examples 24 through 26, 29 through 34) that exhibits superior antifungal activities to the fungi such as Asp., Pen., Cla., Aur., Cl., Tri., and Pae. In addition, it is the compound in which $R_5$ is a hydrogen atom or a linear $C_{1-8}$ alkyl group and $R_6$ is a hydrogen atom (i.e., the compounds in Examples 24 through 26, 29 through 34) that exhibits superior antifungal activities to the wood rot fungi (e.g., Tyr., and Cor.) [Table 9].

(9) The compound (Ib) in which $R_5$ is a phenyl group substituted by chlorine, a trifluoromethyl group or a nitro group and $R_6$ is a hydrogen atom (i.e., the compounds in Examples 38 through 42) exhibits superior antibacterial and antifungal activities to the grampositive bacteria (e.g., Sta., and Bac.), the fungus [the yeast (e.g., Sac., and Can.), Asp., Pen., Cla., Aur., Cha., Tri., and Pae., and the wood rot fungi (e.g., Tyr., and Cor.)] [Table 10].

(10) The compound (Ib) in which $R_5$ and $R_6$ are each a methyl group, or $R_5$ and $R_6$ form a 1-piperidyl group in cooperation with a nitrogen atom adjacent thereto (i.e., the compounds in Examples 44 and 46) exhibits superior antibacterial and antifungal activities to the gram-positive bacteria (e.g., Sta., and Bac.) the fungus [preferably, those other than the yeast (e. g., Asp., Pen., Cla., Aur., Cha., and Pac.), and the wood rot fungi (e. g., Tyr., and Cor.) ] [Table 11].

What is claimed is:

1. A compound represented by the general formula:

$$Br-C\equiv C-CO-NR_5R_6 \qquad (Ib)$$

wherein $R_5$ and $R_6$ are each a hydrogen atom, or an optionally substituted hydrocarbon group selected from a $C_{1-24}$ alkyl group, a $C_{3-8}$ cycloalkyl group, and a $C_{6-18}$ aryl group.

2. A compound as claimed in claim 1 wherein the optionally substituted hydrocarbon group represented by $R_5$ and $R_6$ is (i) a linear or branched $C_{1-24}$ alkyl group, the $C_{1-24}$ alkyl group being optionally substituted by 1 through 4 substituents selected from the group consisting of (1) halogen, and (2) nitro;

(ii) a $C_{3-8}$ cycloalkyl group, the $C_{3-8}$ cycloalkyl group being optionally substituted by 1 through 4 substituents selected from the group consisting of (1) $C_{1-4}$ alkyl, (2) halogen and (3) nitro; or (iii) a $C_{6-18}$ aryl group, the $C_{6-18}$ aryl group being optionally substituted by 1 through 4 substituents selected from the group consisting of (1) a $C_{1-4}$ alkyl group as optionally substituted by a halogen atom, (2) halogen and (3) nitro.

3. A compound as claimed in claim 1 wherein $R_5$ is an optionally substituted linear $C_{1-18}$ alkyl group or an optionally substituted phenyl group.

4. A compound as claimed in any one of claims 1 through 3 wherein $R_6$ is a hydrogen atom.

5. A compound as claimed in claim 1 wherein $R_5$ and $R_6$ are each a hydrogen atom.

6. A compound as claimed in claim 1 wherein $R_5$ is a $C_{1-8}$ alkyl group and $R_6$ is a hydrogen atom.

7. A compound as claimed in claim 1 wherein $R_5$ is a $C_{1-8}$ alkyl group, the $C_{1-8}$ alkyl group being optionally substituted by 1 through 4 substituents selected from the group consisting of (1) $C_{3-8}$ cycloalkyl, (2) halogen and (3) nitro and $R_6$ is a hydrogen atom.

8. A compound as claimed in claim 1 wherein $R_5$ is a $C_{1-18}$ alkyl group, and $R_6$ is a $C_{1-18}$ alkyl group.

9. A compound as claimed in claim 1 wherein $R_5$ is a $C_{1-6}$ alkyl group, and R6 is a $C_{1-6}$ alkyl group.

10. A compound as claimed in claim 1 wherein R5 is a $C_{6-18}$ aryl group, the $C_{6-18}$ aryl group being optionally substituted by 1 through 4 substituents selected from the group consisting of (1) a $C_{1-4}$ alkyl group, the $C_{1-4}$ alkyl group being optionally substituted by a halogen atom, (2) halogen and (3) nitro, and R6 is a hydrogen atom.

11. A compound as claimed in claim 1 wherein R5 is a phenyl group optionally substituted by halogen, trifluoromethyl, or nitro, and $R_6$ is a hydrogen atom.

12. A compound as claimed in claim 1 wherein $R_5$ is a $C_{3-8}$ cycloalkyl group, and $R_6$ is a hydrogen atom.

13. A compound as claimed in claim 1 wherein the compound is N-(tert-butyl)-3-bromopropiolamide, N-(n-hexyl)-3-bromopropiolamide, N-(n-heptyl)-3-bromopropiolamide, N-(n-octyl )- 3-bromopropiolamide, N-(n-nonyl)-3-bromopropiolamide, N-(n-decyl)- 3-bromopropiolamide, 3-bromopropiolamide, N-methyl-3-bromopriopiolamide, N-ethyl-3-bromopropiolamide, N-propyl-3-bromopropiolamide, N-butyl-3-bromopropiolamide, N-pentyl-3-bromopropiolamide, N-dodecyl-3-bromopropiolamide, N-tetradecyl-3-bromopriopiolamide, N-octadecyl-3-bromopropiolamide, N-(m-chlorophenyl)-3-bromopropiolamide, N-(p-chlorophenyl)-3-bromopropiolamide, N-(m-trifluoromethylphenyl)-3-bromopropiolamide, N-(m-nitrophenyl)-3-bromopropiolamide, N-(2,4-dichlorophenyl)-3-bromopropiolamide, [N-(2-pyridyl(ethyl))-3-bromopropiolamide,] N,N-dimethyl-3-bromopropiolamide, N,N-dibutyl- 3-bromopropiolamide, [1-(3-bromopropioloyl) piperidine,] or N-cyclohexyl-3-bromopropiolamide.

14. A composition for controlling noxious organisms which comprises a compound represented by the general formula:

$$Br-C\equiv C-CO-R_5R_6 \qquad (Ib)$$

wherein $R_5$ and $R_6$ are each a hydrogen atom or an optionally substituted hydrocarbon group.

15. A composition for controlling noxious organisms comprising a compound claimed in any one of claims 1 through 12 and 13.

16. The composition for controlling noxious organisms as claimed in claim 14 wherein the composition is an antiblastic composition, an antifungal composition, an insecticide, an acaricide or a termiticide.

17. The composition for controlling noxious organisms as claimed in claim 14 wherein the composition is a composition for preventing deterioration of wood.

18. The composition for controlling noxious organisms as claimed in claim 14 wherein the composition is an antideterioration for industrial water.

19. An antibacterial composition that kills or inhibits the growth of gram-positive bacterium, which comprises the compound claimed in claim 1 wherein $R_5$ is a hydrogen atom or a linear alkyl group, and $R_6$ is a hydrogen atom.

20. An antibacterial composition that kills or inhibits the growth of gram-negative bacterium, which comprises the compound claimed in claim 1 wherein $R_5$ is a hydrogen atom or a methyl group, and $R_6$ is a hydrogen atom.

21. An antifungal composition which comprises the compound claimed in claim 1 wherein $R_5$ is a hydrogen atom or a linear alkyl group, and $R_6$ is a hydrogen atom.

22. An antibacterial composition that kills or inhibits the growth of gram-positive bacterium, which comprises the compound claimed in claim 1 wherein $R_5$ is a phenyl group substituted by chlorine, a trifluoromethyl group, or a nitro group, and $R_6$ is a hydrogen atom.

23. An antifungal composition which comprises the compound claimed in claim 1 wherein $R_5$ is a phenyl group substituted by chlorine, a trifluoromethyl group or a nitro group, and $R_6$ is a hydrogen atom.

24. An antibacterial composition that kills or inhibits the growth of gram-positive bacterium, which comprises the compound claimed in claim 1 wherein $R_5$ and $R_6$ are each a methyl group.

25. An antifungal composition which comprises the compound claimed in claim 1 wherein $R_5$ and $R_6$ are each a methyl group.

26. A method of controlling noxious organisms comprising the step of applying an effective amount of a compound represented by the general formula:

$$Br-C\equiv C-CONR_5R_6 \qquad (Ib)$$

wherein $R_5$ and $R_6$ are each a hydrogen atom or an optionally substituted hydrocarbon group.

27. A method of controlling noxious organisms comprising the step of applying an effective amount of a compound claimed in any one of claims 1 through 12 or 13.

28. The composition for controlling noxious organisms as claimed in claim 15 wherein the composition is an antiblastic composition, an antifungal composition, an insecticide, an acaricide or a termiticide.

29. The composition for controlling noxious organisms as claimed in claim 15 wherein the composition is a composition for preventing deterioration of wood.

30. The composition for controlling noxious organisms as claimed in claim 15 wherein the composition is an antideterioration for industrial water.

* * * * *